(12) United States Patent
Santini, Jr. et al.

(10) Patent No.: US 7,445,766 B2
(45) Date of Patent: Nov. 4, 2008

(54) MEDICAL DEVICE AND METHOD FOR DIAGNOSTIC SENSING

(75) Inventors: John T. Santini, Jr., Bedford, MA (US); Norman F. Sheppard, Jr., Bedford, MA (US)

(73) Assignee: MicroCHIPS, Inc., Bedford, MA (US)

( * ) Notice: Subject to any disclaimer, the term of this patent is extended or adjusted under 35 U.S.C. 154(b) by 0 days.

(21) Appl. No.: 11/279,227

(22) Filed: Apr. 10, 2006

(65) Prior Publication Data

US 2006/0171888 A1 Aug. 3, 2006

Related U.S. Application Data

(60) Division of application No. 11/039,048, filed on Jan. 19, 2005, now abandoned, which is a continuation of application No. 10/324,556, filed on Dec. 19, 2002, now Pat. No. 6,849,463, which is a continuation of application No. 09/798,562, filed on Mar. 2, 2001, now Pat. No. 6,551,838.

(60) Provisional application No. 60/186,545, filed on Mar. 2, 2000.

(51) Int. Cl.
*A61K 49/00* (2006.01)
(52) U.S. Cl. .............................. 424/9.1; 435/6; 435/7.1; 435/287.1; 436/518; 600/300; 600/309; 600/310
(58) Field of Classification Search ...................... 435/6, 435/7.1, 7.92–7.94, 287.1, 287.2, 288.4; 436/501, 518, 524, 164; 422/58, 101; 600/300, 600/309, 310; 604/891.1; 424/9.1
See application file for complete search history.

(56) References Cited

U.S. PATENT DOCUMENTS

| | | | |
|---|---|---|---|
| 3,692,027 A | 9/1972 | Ellinwood, Jr. | |
| 3,921,636 A | 11/1975 | Zaffaroni | |
| 3,952,741 A | 4/1976 | Baker | |
| 4,003,379 A | 1/1977 | Ellinwood, Jr. | |
| 4,360,019 A | 11/1982 | Portner et al. | |
| 4,507,115 A | 3/1985 | Kambara et al. | |
| 4,585,652 A | 4/1986 | Miller et al. | |
| 4,731,049 A | 3/1988 | Parsi | |
| 4,731,051 A | 3/1988 | Fischell | |
| 4,793,825 A | 12/1988 | Benjamin et al. | |
| 4,865,813 A * | 9/1989 | Leon | 422/101 |
| 4,874,500 A | 10/1989 | Madou | |
| 4,919,666 A | 4/1990 | Buchhorn | |
| 5,041,107 A | 8/1991 | Heil, Jr. | |
| 5,042,975 A | 8/1991 | Chien et al. | |
| 5,102,402 A | 4/1992 | Dror et al. | |
| 5,143,066 A * | 9/1992 | Komives et al. | 600/317 |
| 5,147,297 A | 9/1992 | Myers et al. | |
| 5,167,625 A | 12/1992 | Jacobsen et al. | |
| 5,170,801 A | 12/1992 | Casper et al. | |
| 5,196,002 A | 3/1993 | Hanover et al. | |
| 5,200,051 A | 4/1993 | Cozzette et al. | |
| 5,252,294 A | 10/1993 | Kroy et al. | |
| 5,254,081 A | 10/1993 | Maurer et al. | |
| 5,261,870 A * | 11/1993 | Hammerstedt et al. | 600/35 |
| 5,279,607 A | 1/1994 | Schentag et al. | |
| 5,304,293 A | 4/1994 | Tierney et al. | |
| 5,318,557 A | 6/1994 | Gross | |
| 5,324,316 A | 6/1994 | Schulman et al. | |
| 5,336,213 A | 8/1994 | D'Angelo et al. | |
| 5,366,454 A | 11/1994 | Currie et al. | |
| 5,368,588 A | 11/1994 | Bettinger | |
| 5,368,704 A | 11/1994 | Madou et al. | |
| 5,380,272 A | 1/1995 | Gross | |
| 5,387,419 A | 2/1995 | Levy et al. | |
| 5,427,585 A | 6/1995 | Bettinger | |
| 5,429,822 A | 7/1995 | Gresser et al. | |
| 5,443,508 A | 8/1995 | Giampapa | |
| 5,449,382 A | 9/1995 | Dayton | |
| 5,474,527 A | 12/1995 | Bettinger | |
| 5,490,962 A | 2/1996 | Cima et al. | |
| 5,493,177 A | 2/1996 | Muller et al. | |
| 5,504,026 A | 4/1996 | Kung | |
| 5,518,680 A | 5/1996 | Cima et al. | |

(Continued)

FOREIGN PATENT DOCUMENTS

DE 29 11 558 A1 9/1980

(Continued)

OTHER PUBLICATIONS

Armani, et al., "Microfabrication Technology for Polycaprolactone, a Biodegradable Polymer," *J. Micromech. Microeng.* 10: 80-84 (2000).

(Continued)

*Primary Examiner*—Long V. Le
*Assistant Examiner*—Gary W Counts
(74) *Attorney, Agent, or Firm*—Sutherland Asbill & Brennan LLP

(57) ABSTRACT

Devices are provided for use in medical diagnostics which include a substrate, a plurality of discrete reservoirs located in the substrate, each reservoir having at least one opening, at least one diagnostic substance contained in each reservoir, and at least one non-degradable barrier layer covering each reservoir opening, the barrier layer being permeable to an agent to be detected, wherein the diagnostic substance remains inside the reservoirs and can react with the agent to be detected.

22 Claims, 8 Drawing Sheets

U.S. PATENT DOCUMENTS

| | | |
|---|---|---|
| 5,533,995 A | 7/1996 | Corish et al. |
| 5,585,069 A | 12/1996 | Zanzucchi et al. |
| 5,605,662 A | 2/1997 | Heller et al. |
| 5,609,629 A | 3/1997 | Fearnot et al. |
| 5,651,900 A | 7/1997 | Keller et al. |
| 5,660,680 A | 8/1997 | Keller |
| 5,662,689 A | 9/1997 | Elsberry et al. |
| 5,707,385 A | 1/1998 | Williams |
| 5,769,884 A | 6/1998 | Solovay |
| 5,770,076 A | 6/1998 | Chu et al. |
| 5,782,799 A | 7/1998 | Jacobsen et al. |
| 5,792,048 A | 8/1998 | Schaefer |
| 5,797,898 A | 8/1998 | Santini, Jr. et al. |
| 5,798,042 A | 8/1998 | Chu et al. |
| 5,824,204 A | 10/1998 | Jerman |
| 5,842,787 A | 12/1998 | Kopf-Sill et al. |
| 5,843,172 A | 12/1998 | Yan |
| 5,843,767 A | 12/1998 | Beattie |
| 5,869,004 A | 2/1999 | Parce et al. |
| 5,872,010 A | 2/1999 | Karger et al. |
| 5,873,904 A | 2/1999 | Ragheb et al. |
| 5,879,697 A | 3/1999 | Ding et al. |
| 5,891,108 A | 4/1999 | Leone |
| 5,893,840 A | 4/1999 | Hull et al. |
| 5,893,974 A | 4/1999 | Keller et al. |
| 5,900,160 A | 5/1999 | Whitesides et al. |
| 5,938,923 A | 8/1999 | Tu et al. |
| 5,947,893 A | 9/1999 | Agrawal |
| 5,948,255 A | 9/1999 | Keller et al. |
| 5,949,187 A | 9/1999 | Xu et al. |
| 5,951,881 A | 9/1999 | Rogers et al. |
| 5,962,081 A | 10/1999 | Ohman et al. |
| 5,971,931 A | 10/1999 | Raff |
| 5,972,027 A | 10/1999 | Johnson |
| 5,976,336 A | 11/1999 | Dubrow et al. |
| 5,985,328 A | 11/1999 | Chu et al. |
| 5,989,445 A | 11/1999 | Wise et al. |
| 6,001,090 A | 12/1999 | Lenhart |
| 6,027,695 A | 2/2000 | Oldenburg et al. |
| 6,042,710 A | 3/2000 | Dubrow |
| 6,051,017 A | 4/2000 | Loeb et al. |
| 6,056,734 A | 5/2000 | Jacobsen et al. |
| 6,066,163 A | 5/2000 | John |
| 6,068,752 A | 5/2000 | Dubrow et al. |
| 6,071,305 A | 6/2000 | Brown et al. |
| 6,081,736 A | 6/2000 | Colvin et al. |
| 6,083,763 A | 7/2000 | Balch |
| 6,096,070 A | 8/2000 | Ragheb et al. |
| 6,096,656 A | 8/2000 | Matzke et al. |
| 6,099,561 A | 8/2000 | Alt |
| 6,114,658 A | 9/2000 | Roth et al. |
| 6,123,861 A | 9/2000 | Santini, Jr. et al. |
| 6,129,685 A | 10/2000 | Howard et al. |
| 6,136,212 A | 10/2000 | Mastrangelo et al. |
| 6,161,047 A | 12/2000 | King et al. |
| 6,163,720 A | 12/2000 | Gyory et al. |
| 6,171,850 B1 | 1/2001 | Nagle et al. |
| 6,178,349 B1 | 1/2001 | Kieval |
| 6,185,455 B1 | 2/2001 | Loeb et al. |
| 6,197,013 B1 | 3/2001 | Reed et al. |
| 6,214,032 B1 | 4/2001 | Loeb et al. |
| 6,232,150 B1 | 5/2001 | Lin et al. |
| 6,241,762 B1 | 6/2001 | Shanley |
| 6,245,104 B1 | 6/2001 | Alt |
| 6,248,540 B1 | 6/2001 | Weinberg et al. |
| 6,251,688 B1 | 6/2001 | Erb et al. |
| 6,253,443 B1 | 7/2001 | Johnson |
| 6,256,522 B1 * | 7/2001 | Schultz ............... 600/317 |
| 6,261,584 B1 | 7/2001 | Peery et al. |
| 6,273,908 B1 | 8/2001 | Ndondo-Lay |
| 6,273,913 B1 | 8/2001 | Wright et al. |
| 6,287,628 B1 | 9/2001 | Hossainy |
| 6,288,888 B1 | 9/2001 | Sakata et al. |
| 6,289,237 B1 | 9/2001 | Mickle et al. |
| 6,306,420 B1 | 10/2001 | Cheikh |
| 6,319,241 B1 | 11/2001 | King et al. |
| 6,331,439 B1 | 12/2001 | Cheruki et al. |
| 6,334,856 B1 | 1/2002 | Allen et al. |
| 6,334,859 B1 | 1/2002 | Richter |
| 6,349,232 B1 | 2/2002 | Gordon |
| 6,361,522 B1 | 3/2002 | Scheiner et al. |
| 6,364,856 B1 | 4/2002 | Ding et al. |
| 6,379,382 B1 | 4/2002 | Yang |
| 6,384,353 B1 | 5/2002 | Huang et al. |
| 6,387,121 B1 | 5/2002 | Alt |
| 6,391,052 B2 | 5/2002 | Buirge et al. |
| 6,395,326 B1 | 5/2002 | Castro |
| 6,436,853 B2 | 8/2002 | Lin et al. |
| 6,480,730 B2 | 11/2002 | Darrow et al. |
| 6,491,666 B1 | 12/2002 | Santini, Jr. et al. |
| 6,527,762 B1 | 3/2003 | Santini, Jr. et al. |
| 6,530,951 B1 | 3/2003 | Bates et al. |
| 6,537,256 B2 | 3/2003 | Santini, Jr. et al. |
| 6,551,838 B2 | 4/2003 | Santini, Jr. et al. |
| 6,555,278 B1 | 4/2003 | Santini, Jr. et al. |
| 6,558,422 B1 | 5/2003 | Baker |
| 6,562,065 B1 | 5/2003 | Shanley |
| 6,571,125 B2 | 5/2003 | Thompson |
| 6,587,719 B1 | 7/2003 | Barrett et al. |
| 6,596,296 B1 | 7/2003 | Nelson et al. |
| 6,638,302 B1 | 10/2003 | Curcio |
| 6,652,582 B1 | 11/2003 | Stinson |
| 6,656,162 B2 | 12/2003 | Santini, Jr. et al. |
| 6,663,615 B1 | 12/2003 | Madou et al. |
| 6,666,821 B2 | 12/2003 | Keimel |
| 6,669,683 B2 | 12/2003 | Santini, Jr. et al. |
| 6,673,596 B1 * | 1/2004 | Sayler et al. ............. 435/288.7 |
| 6,709,379 B1 | 3/2004 | Brandau et al. |
| 6,730,072 B2 | 5/2004 | Shawgo et al. |
| 6,733,485 B1 | 5/2004 | Whitehurst et al. |
| 6,757,560 B1 | 6/2004 | Fischer et al. |
| 6,773,429 B2 | 8/2004 | Sheppard, Jr. et al. |
| 6,783,543 B2 | 8/2004 | Jang |
| 6,808,522 B2 | 10/2004 | Richards et al. |
| 6,827,250 B2 | 12/2004 | Uhland et al. |
| 6,908,770 B1 | 6/2005 | McDevitt et al. |
| 6,968,743 B2 | 11/2005 | Rich et al. |
| 7,010,345 B2 | 3/2006 | Hill et al. |
| 7,025,760 B2 | 4/2006 | Miller et al. |
| 2001/0034550 A1 | 10/2001 | Buirge et al. |
| 2001/0053885 A1 | 12/2001 | Gielen et al. |
| 2002/0007215 A1 | 1/2002 | Falotico et al. |
| 2002/0022826 A1 | 2/2002 | Reynolds et al. |
| 2002/0038137 A1 | 3/2002 | Stein |
| 2002/0038146 A1 | 3/2002 | Harry |
| 2002/0055761 A1 | 5/2002 | Mann et al. |
| 2002/0072784 A1 | 6/2002 | Sheppard, Jr. et al. |
| 2002/0082665 A1 | 6/2002 | Hialler et al. |
| 2002/0099359 A1 | 7/2002 | Santini, Jr. et al. |
| 2002/0107470 A1 | 8/2002 | Richards et al. |
| 2002/0107553 A1 | 8/2002 | Hill et al. |
| 2002/0111601 A1 | 8/2002 | Thompson |
| 2002/0143369 A1 | 10/2002 | Cohn et al. |
| 2002/0165586 A1 | 11/2002 | Hill et al. |
| 2002/0183721 A1 | 12/2002 | Santini, Jr. et al. |
| 2002/0187260 A1 | 12/2002 | Sheppard, Jr. et al. |
| 2002/0188282 A1 | 12/2002 | Greenberg |
| 2003/0004549 A1 | 1/2003 | Hill et al. |
| 2003/0032946 A1 | 2/2003 | Fishman |
| 2003/0055344 A1 | 3/2003 | Eigier et al. |
| 2003/0055345 A1 | 3/2003 | Eigler et al. |
| 2003/0069560 A1 | 4/2003 | Adamis et al. |
| 2003/0104590 A1 | 6/2003 | Santini, Jr. et al. |
| 2003/0105455 A1 | 6/2003 | Santini, Jr. et al. |

| | | | |
|---|---|---|---|
| 2003/0108659 | A1 | 6/2003 | Bales |
| 2004/0106953 | A1 | 6/2004 | Yomtov et al. |
| 2004/0243241 | A1 | 12/2004 | Istephanous |
| 2004/0254635 | A1 | 12/2004 | Shanley et al. |
| 2005/0049472 | A1 | 3/2005 | Manda et al. |
| 2005/0055080 | A1 | 3/2005 | Istephanous |
| 2005/0100937 | A1 | 5/2005 | Holmes |
| 2005/0203608 | A1 | 9/2005 | Shanley |
| 2005/0203609 | A1 | 9/2005 | Shanley |

FOREIGN PATENT DOCUMENTS

| | | |
|---|---|---|
| DE | 39 08 822 A1 | 9/1990 |
| DE | 296 998 A5 | 12/1991 |
| DE | 197 16 683 C1 | 6/1998 |
| EP | 0 347 579 A2 | 12/1989 |
| EP | 0850604 A2 | 1/1998 |
| WO | WO 93/03790 A1 | 3/1993 |
| WO | WO 98/00107 | 1/1998 |
| WO | WO 98/23228 A1 | 6/1998 |
| WO | WO 98/26814 | 6/1998 |
| WO | WO 98/46325 A1 | 10/1998 |
| WO | WO 99/03684 A1 | 1/1999 |
| WO | WO 99/09960 | 3/1999 |
| WO | WO 99/16500 A2 | 4/1999 |
| WO | WO 99/92590 | 10/1999 |
| WO | WO 99/55396 A1 | 11/1999 |
| WO | WO 02/056862 A1 | 7/2002 |
| WO | WO 02/058678 A2 | 8/2002 |

OTHER PUBLICATIONS

Bae, et al., "Pulsatile Drug Release by Electric Stimulus," *ACS Symp. Series Polymeric Drugs & Drug Admin.*, pp. 99-110 (1994).

Becker, et al., "Hot Embossing as a Method for the Fabrication of Polymer High Aspect Ration Structures," *Sensors and Actuators.* 83:130-135 (2000).

Becker, et al., "Polymer Microfabrication Methods for Microfluidic Analytical Methods," *Electrophoresis*, 21:12-26 (2000).

Becker, et al., "Planar Quartz Chips with Submicron Channels for Two-Dimensional Capillary Electrophoresis Applications," *J. Micromech Microeng.* 8:24-28 (1998).

Becker, et al., "Polymer Nanowell Plates with Variable Well Slope Angles," In *Microreaction Technology: Industrial Prospects, Proceedings 3rd Int'l Conf. Microreaction Tech.* (Ehrfeld, ed.), Springer 2000.

Becker, et al., "Polymer Microfluidics: The Technology Chain," in *Microfluidic Devices and Systems III, Proceedings of SPIE* vol. 4177 (Mastrangelo, et al., eds.) (2000).

Becker, et al., "Microfluidic Manifolds by Polymer Hot Embossing for μ-TAS Applications," in Proceedings of the μ-TAS '98 Workshop, Harrison & Van Den Berg eds., Oct. 13-16, 1998.

Bhattacharya & Tummala, "Next Generation Integral Passives: Materials, Processes, and Integration of Resistors and Capacitors on PWB substrates," *J. Mater. Sci.-Mater. Electron.* 11(3):253-68 (2000).

Bremus-Kobberling, et al., "Laser Microperforation of a Retina Implant," *MICRO.tec 2000, Conference Proceedings*, vol. 1, Hannover, Germany (Sep. 25-27, 2000).

Ehrick, et al., "Artificial Muscle-Based Microactuators for Reversible Controlled Release" ACS Abstracts, No. 22, 222nd ACS Nat;l Meeting (Chicago 2001).

Frankenthal, et al., "Electroetching of Platinum in the Titanium-Platinum-Gold Metallization on Silicon Integrated Circuits", *J. Electrochem. Soc.*, May 1976.

Goretty, et al., "Microdevices Fabricated by Hot Embossing," *ACS Abstracts*, No. 468 (Mar. 26-30, 2000).

Grayson, et al., "A BioMEMS Review: MEMS Technology for Physiologically Integrated Devices", Proceedings of the IEEE, vol. 92, No. 1, Jan. 2004, pp. 6-21.

Grayson, et al., "Multi-Pulse Drug Delivery From A Resorbable Polymeric Microchip Device", Nature Materials, vol. 2, Nov. 2003, pp. 767-772.

Izumi, et al., "Activation of a Gold Electrode by Electrochemical Oxidation-Reduction Pretreatment In Hydrochloric Acid", *J. Electroanal. Chem.* 303: 151-60 (1991).

Jackman, et al., "Fabricating Large Arrays of Microwells with Arbitrary Dimension and Filling Them Using Discontinuous Dewetting," *Anal. Chem.* 70: 2280-2287 (1998).

Kano, et al., "Fundamentals and Practices of Mediated Bioelectrocatalysis," *Analytical Sciences* 16: 1013-21 (2000).

Kwon, et al., "Electrically Erodible Polymer Gel For Controlled Release of Drugs," *Nature* 354: 291-93 (1991).

Low, et al., "Microactuators Towards Microvalves for Responsive Controlled Drug Delivery," *Sensors & Actuators B.* 67:149-60(2000).

Liu C., et al. "Applications of Microfabrication and Micromachining Techniques to Biotechnology," *Trends in Biotechnology*, vol. 15, No. 6, pp. 213-216 (1997).

Madou, et al., "Exploitation of a Novel Artificial Muscle for Controlled Drug Delivery," pp. 495-497 (1999).

Madou & Florkey, "From Batch to Continuous Manufacturing of Microbiomedical Devices," *Chem. Rev.*, 100: 2679-92 (2000).

Madou, "Fundamentals of Microfabrication," pp. 468-512 (CRC Press 1997).

McCormick, et al., "Microchannel Electrophoretic Separations of DNA in Injection-Molded Plastic Substrates," Analytical Chemistry. 69:2626-2630 (1997).

Santini, et al., "Microchips as Controlled Drug-Delivery Devices," *Angew Chem. Int. Ed. Engl* 39(14): 2396-407 (2000).

Santini, et al. "Microchip Technology in Drug Delivery," *Ann. Med.* 32(6) 377-79 (2001).

Santini, et al. "A Controlled-Release Microchip," Nature 397:335-38 (1999).

Sassi, et al., "Electrophoresis of DNA in Novel Thermoreversible Matrices," *Electrophoresis.* 17:1460-69 (1996).

Schaefer, "Pulsatile Parathyroid Hormones Secretion in Health and Disease," *Novartis Found. Symp.* 2000; 227:225-39 (abstract).

Schwarz, et al., "Micro Implantable Visual Prosthesis," *1st Ann. Intl. IEEE-EMBS Spec. Topic Conf. Microtech. Medicine & Biology*, pp. 461-465, (Lyon, France, Oct. 2000).

Shawgo, et al., "BioMEMS for Drug Deliver", *Current Opinion in Solid State and Materials Science*, May 8, 2002, pp. 329-334.

Surbled, et al., "Characterization of Sputtered TiNi Shape Memory Alloy Thin Films," *Japanese Journal of Applied Physics*, 38: L1547-L1549 (1999).

Surbled, et al., "Shape Memory Alloys for Micromembranes Actuation," *SPIE.* 3825:63-70 (1999).

Surbled, et al., "Array of Shape Memory Alloy One-Shot Micro-Valves for Drug Delivery," *MME '99, Gif sur Yvette*, France (Sep. 27-28, 1999).

Tierney, et al., "New Electrorelease Systems Based on Microporous Membranes," *J. Electrochem. Soc.*, 137:3789-3793 (1990).

Tierney, et al., "Electroreleasing Composite Membranes for Delivery of Insulin and Other Biomacromolecules," *J. Electrochem. Soc.*, 137:2005-2006 (1990).

Uhrich, et al., "Synthesis and Characterization of Degradable Poly(anhydride-co-imides)," *Macromolecules* 28:2184-2193 (1995).

Vladimirsky, et al., "Thin Metal Film Thermal Micro-Sensors," *Proc. SPIE-Int. Soc. Eng.* 2640:184-92 (1995).

Wogersien, et al., "Fabrication of Thin Film Resistors and Silicon Microstructures Using a Frequency Doubled Nd:YAG-Laser," *Proc. SPIE-Int. Soc. Opt. Eng.* 3680:1105-12 (1999).

* cited by examiner

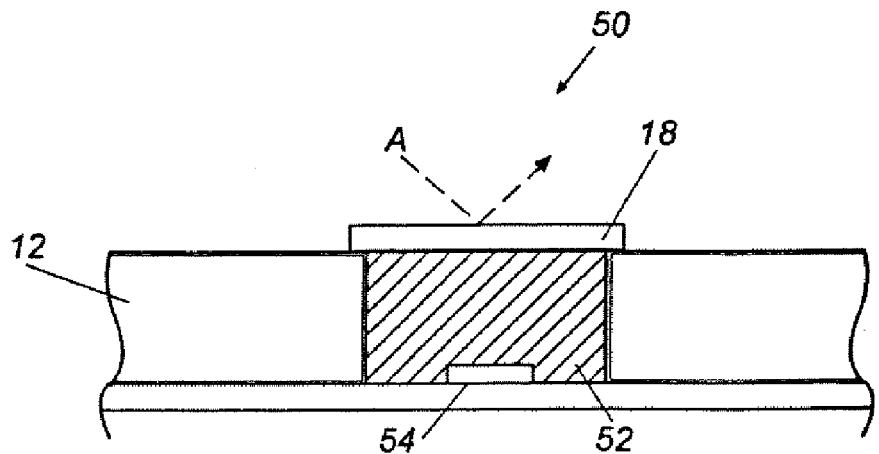
Fig. 8A
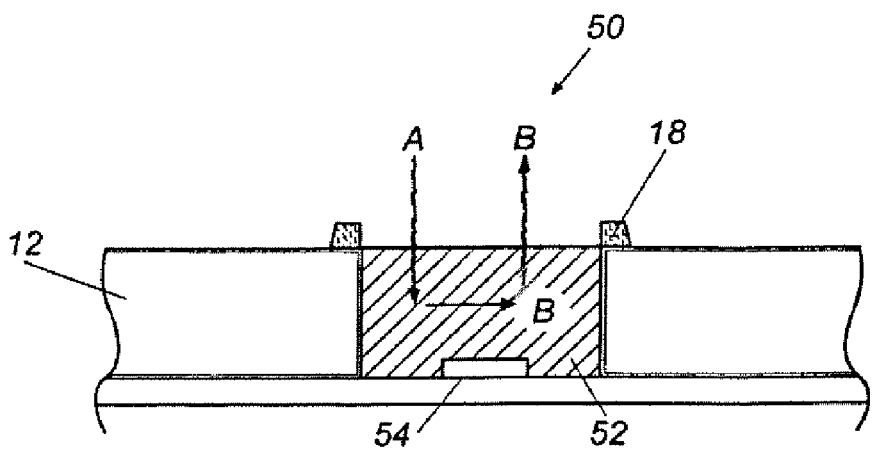
Fig. 8B
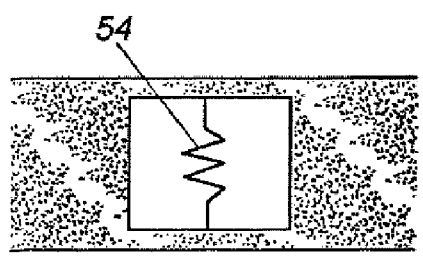 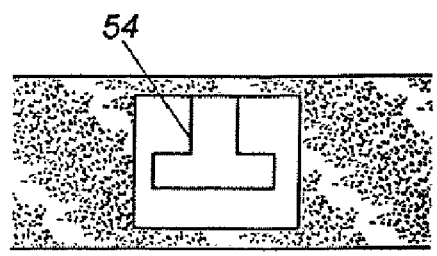
Fig. 8C          Fig. 8D

MEDICAL DEVICE AND METHOD FOR DIAGNOSTIC SENSING

CROSS-REFERENCE TO RELATED APPLICATIONS

This is a divisional of U.S. application Ser. No. 11/039,048, filed Jan. 19, 2005 now abandoned, which is a continuation of U.S. application Ser. No. 10/324,556, filed Dec. 19, 2002, now U.S. Pat. No. 6,849,463, which is a continuation of U.S. application Ser. No. 09/798,562, filed Mar. 2, 2001, now U.S. Pat. No. 6,551,838, which claims benefit of U.S. Provisional Application No. 60/186,545, filed Mar. 2, 2000.

BACKGROUND OF THE INVENTION

This invention is in the field of miniaturized devices having reservoirs which contain small devices or device components and/or chemicals.

Microarray systems have been developed that analyze numerous compounds, such as for drug activity or hybridization analysis of nucleotide molecule sequences. For example, U.S. Pat. No. 5,843,767 to Beattie discloses a microfabricated, flowthrough "genosensors" for the discrete detection of binding reactions. The apparatus includes a nanoporous glass wafer having tapered wells in which nucleic acid recognition elements are immobilized. U.S. Pat. No. 6,083,763 to Balch discloses an apparatus for analyzing molecular structures within a sample substance using an array having a plurality of test sites upon which the sample substance is applied. The test sites typically are in microplate arrays, such as microtitre plates. These apparatuses, however, do not provide any means for sealing one or more of the wells or for selectively exposing one or more of the wells, for example, on demand or upon passive exposure to certain conditions.

U.S. Pat. Nos. 5,797,898 and 6,123,861 to Santini, et al. describe microchip devices that release drug molecules from reservoirs having reservoir caps that actively or passively disintegrate. It would be advantageous to adapt these devices for use in sensing applications and for use in initiating or measuring chemical reactions in a micro-scale area or volume at specific points in time.

U.S. Pat. No. 5,252,294 to Kroy discloses micromechanical structures having closed cavities for use in storage and handling of substances, for example, in research and testing of the substances. There is no disclosure, however, of selectively controlling exposure of individual cavities without microvalves, nor is there any disclosure of isolating individual sensing means.

It would be desirable to provide miniaturized devices for use in initiating and controlling chemical reactions, analyses, or measurements in a micro-scale area or volume, at specific points in time. It would also be desirable to provide methods of making and using such miniaturized devices.

SUMMARY OF THE INVENTION

Microchip devices are provided to store and protect chemicals and smaller, secondary devices from environmental exposure until such time as exposure is required, for example, to initiate a chemical reaction and/or to perform an analysis or sensing function. In one embodiment, the microchip device includes a substrate having a plurality of reservoirs which contain the secondary device, and at least one barrier layer covering each reservoir to isolate the secondary device from one or more environmental components outside the reservoirs. The barrier layer can be selectively disintegrated or permeabilized to expose the secondary device to the one or more environmental components. The secondary device preferably includes a sensor or sensing component, for example, a biosensor, or a light detection or imaging device, such as an optical fiber. In one variation, the microchip device further includes a reacting component, such as catalyst or reagent, in one or more reservoirs. Alternatively, the sensor or sensing component can be attached to the substrate outside of the reservoir while a reservoir contains a reacting component.

In another embodiment, the microchip device includes a substrate having a plurality of reservoirs which contain a reacting component, and at least one barrier layer covering each reservoir to isolate the reacting component from one or more environmental components outside the reservoirs. The barrier layer can be selectively disintegrated or permeabilized to expose the reacting component to the one or more environmental components. In a preferred variation, the reacting component is a catalyst or enzyme that remains immobilized in the reservoir even after exposure to the environmental components. In some embodiments, swellable materials and osmotic pressure generating materials can be incorporated into reservoirs for use in generating pressure forces effective to rupture the barrier layer.

The microchip device is used to protect chemicals and devices from exposure to the surrounding environment until the exposure is desired, which is particularly useful when the chemicals or devices within the reservoir are sensitive to environmental conditions, for example, when the devices fail or materials foul following prolonged exposure to the environment. In one embodiment, an easily fouled catalyst used to initiate a desired heterogeneous chemical reaction is sealed inside a reservoir of a microchip device to protect it from the surrounding environment. When it is desired to initiate the reaction, the barrier layer on the reservoir is removed or made permeable. The reagents for the reaction present in the surrounding environment pass into the reservoir (e.g., by diffusion), contact the catalyst, react at the catalyst surface, and the products pass out of the reservoir. This heterogeneous reaction continues until the reagents are exhausted or the catalyst becomes fouled. This process may be repeated numerous times by opening additional reservoirs and exposing fresh catalyst.

In another embodiment, the microchip device includes one or more sensors that are located inside each reservoir. The sensors are protected from the environment until the barrier layer is removed or made permeable. Once the barrier is removed or made permeable, the sensors can detect the presence and/or quantity of molecules or the conditions in or near one or more reservoirs. Such sensors can be used, for example, in controlling and monitoring the release of molecules from other chemical release devices or the release of chemicals from reservoirs in the same device.

BRIEF DESCRIPTION OF THE DRAWINGS

FIGS. 8A-B are cross-sectional diagrams illustrating a device having a reservoir containing a catalytic material, with the intact barrier layer impermeable to reactant A (FIG. 8A) and the barrier layer partially removed and permitting reactant A to contact the catalytic material to yield product B (FIG. 8B). FIGS. 8C and 8D are diagrams illustrating optional elements which can be incorporated into the reservoirs to control the catalytic reactions, such as resistive heaters (FIG. 8C) and polarizable electrodes (FIG. 8D).

DETAILED DESCRIPTION OF THE INVENTION

Figure 1A:
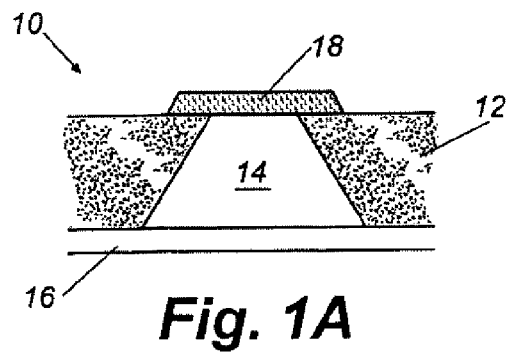
FIGS. 1A-C are cross-sectional diagrams showing various embodiments of a single reservoir of the device, having a barrier layer over the reservoir and on top of the substrate (FIG. 1A), a barrier layer within the opening of the reservoir (FIG. 1B), and a combination thereof in a device having two substrate portions bonded together (FIG. 1C).

Microchip devices are provided that store and protect reacting components and secondary devices from the environment for a period of time until exposure to the environment is desired. The microchip devices, which provide for the selective or controlled exposure of these contents, include a plurality of reservoirs, the contents of which are completely or partially isolated until it is desired to expose a reacting component or secondary device in the reservoir to the environment, or a portion thereof, outside of the reservoir. The devices are designed to restrict, enhance, or otherwise control the passage of molecules or energy into (or out of) the reservoirs. These functions are accomplished by covering at least one opening of each reservoir of the microchip device by at least one barrier layer.

As used herein, a "microchip" is a miniaturized device fabricated using methods commonly applied to the manufacture of integrated circuits and MEMS (MicroElectroMechanical Systems) such as ultraviolet (UV) photolithography, reactive ion etching, and electron beam evaporation, as described, for example, by Wolf & Tauber, *Silicon Processing for the VLSI Era, Volume 1—Process Technology* (Lattice Press, Sunset Beach, Calif., 1986); and Jaeger, *Introduction to Microelectronic Fabrication*, Vol. V in *The Modular Series on Solid State Devices* (Addison-Wesley, Reading, Mass., 1988), as well as MEMS methods that are not standard in making computer microchips, including those described, for example, in Madou, *Fundamentals of Microfabrication* (CRC Press 1997) and micromolding and micromachining techniques known in the art. The microchip fabrication procedure allows the manufacture of devices with primary dimensions (length of a side if square or rectangular, or diameter if circular) ranging from less than a millimeter to several centimeters. A typical device thickness is 500 μm. However, the thickness of the device can vary from approximately 10 μm to several millimeters, depending on the device's application. Total device thickness and reservoir volume can also be increased by bonding or attaching additional silicon wafers or other substrate materials to the fabricated microchip device. In general, changing the device thickness affects the volume of each reservoir and may affect the maximum number of reservoirs that may be incorporated onto a microchip. In vivo applications of the device typically require devices having a primary dimension of 3 cm or smaller for subcutaneous implantation, but may be up to several centimeters for peritoneal or cranial implantation. Devices for in vivo applications are preferably small enough to be swallowed or implanted using minimally invasive procedures. Smaller in vivo devices (on the order of a millimeter) can be implanted using a catheter or other injection means. Microchip devices that remain outside of the body, but that are used in a system for in vivo applications (e.g., sensing following extraction of a sample of biological fluid), have much fewer size restrictions. Devices for in vitro applications also have fewer size restrictions and, if necessary, can be made much larger than the dimension ranges for in vivo devices.

I. Device Components and Materials

Each microchip device includes a substrate having reservoirs containing a reacting component or secondary device, wherein at least one opening of each reservoir is covered by a barrier layer that protects the contents from one or more components of the surrounding environment. Examples of these environmental components include chemicals, water, biological fluids, cells, molecules, and one or more forms of energy, such as light or heat.

Figure 1B:
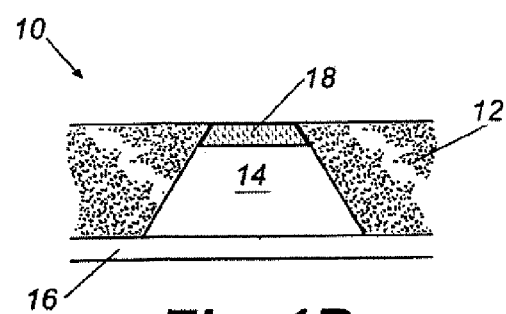
Figure 1C:
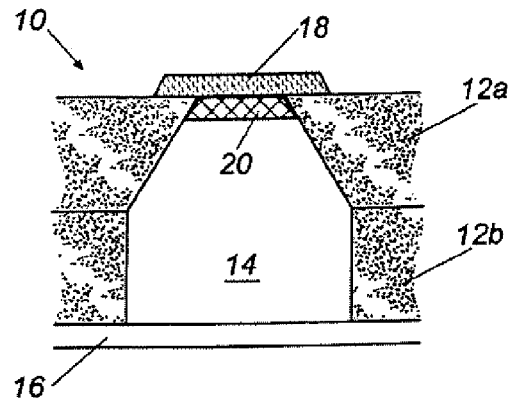

FIGS. 1A-C illustrate a cross-sectional view of various embodiments of microchip device 10 comprising substrate 12, reservoir 14, backing plate 16, and barrier layer 18. In the embodiment of FIG. 1C, the substrate is composed of substrate portions 12a and 12b, and the microchip device further includes semi-permeable barrier layer 20. It should be noted that the backing plate is typically utilized only in device embodiments produced by a process in which reservoirs are formed from a hole that passes completely through the substrate. The backing plate essentially can be any impermeable plate or layer of rigid or flexible material that serves the sealing function.

The microchip devices may be classified as passive devices, in which the permeability of the barrier layer changes without any user intervention, or active devices, in which the device controller initiates an action which renders the barrier layer permeable. Active devices may include control circuitry, memory, and a power source, and may be operable using wireless or remote communication, control, and data and power transmission.

A. The Substrate

The substrate contains the reservoirs and serves as the support for the microchip. Any material which can serve as a support, which is suitable for etching or machining or which can be cast or molded, and which is impermeable to the contents of the reservoir and to the surrounding environment (e.g., water, blood, electrolytes, other solutions, or air) may be used as a substrate. Examples of suitable substrate materials include ceramics, glasses, certain metals, semiconductors, and degradable and non-degradable polymers. Biocompatibility of the substrate material is preferred, but not required. For in vivo applications, non-biocompatible materials may be encapsulated in a biocompatible material, such as poly(ethylene glycol) or polytetrafluoroethylene-like materials, before use. A few examples of strong, non-degradable, easily etched substrates that are impermeable to the molecules or secondary devices contained in the reservoirs and to the surrounding fluids are silicon, glass, and titanium. In another embodiment, the substrate is made of a strong material that degrades or dissolves over a period of time into biocompatible components. This embodiment is preferred for in vivo applications where the device is implanted and physical removal of the device at a later time is not feasible or is difficult, for example, brain implants. An example of a class of strong, biocompatible materials is the poly(anhydride-co-imides) described in Uhrich et al., "Synthesis and characterization of degradable poly(anhydride-co-imides)", *Macromolecules*, 28:2184-93 (1995).

Figure 12A:
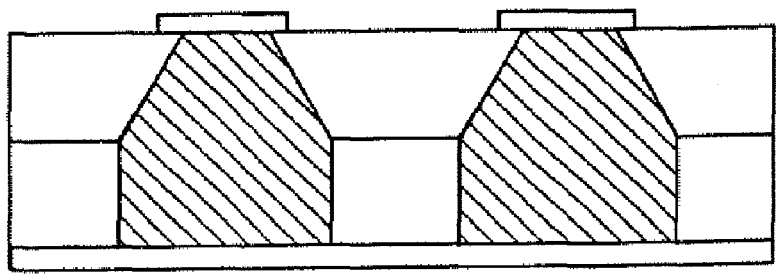
FIGS. 12A-D are cross-sectional diagrams showing reservoirs having complex reservoir shapes, which can be made, for example, by utilizing wafer or other substrate bonding methods or by adapting silicon-on-insulator (SOI) fabrication methods.
Figure 12B:
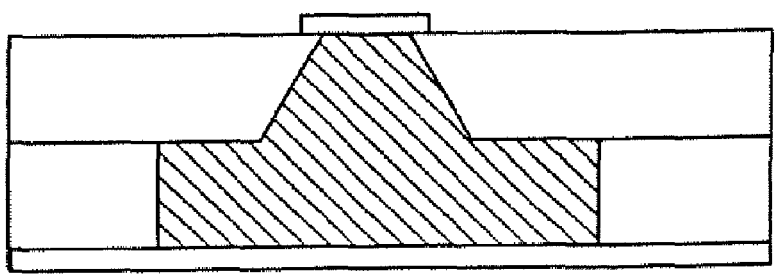
Figure 12C:
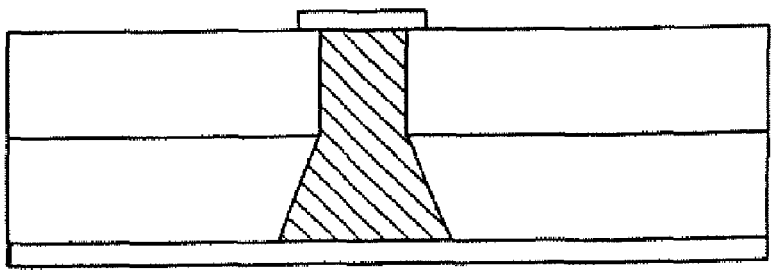
Figure 12D:
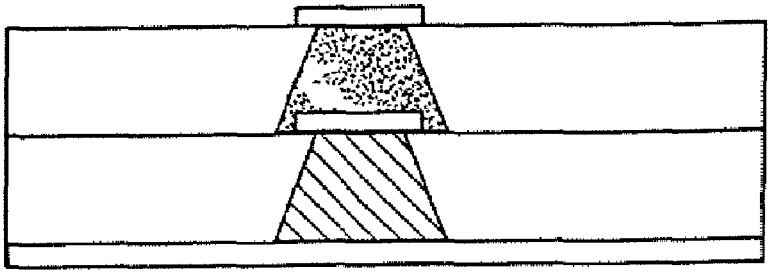

The substrate can be formed of only one material or can be a composite or multi-laminate material, e.g., two or more substrate portions can be bonded together (see FIGS. 12A-C, described below). Multi-portion substrates can be formed of the same or different materials, including for example, silicon, glasses, ceramics, semiconductors, metals, and polymers. Two or more complete microchip devices also can be bonded together to form multi-portion substrate devices (see FIG. 12D).

B. Secondary Devices and Reacting Components

The reservoirs contain secondary devices, reacting components, or combinations thereof, that need to be protected from surrounding environmental components until their exposure is desired.

Second Devices

As used herein, unless explicitly indicated otherwise, the term "secondary device" includes, but is not limited to, any device and component thereof which can be located in or designed to operably communicate with one or more reservoirs in a microchip device. In a preferred embodiment, the secondary device is a sensor or sensing component. As used herein, a "sensing component" includes, but is not limited to, a component utilized in measuring or analyzing the presence, absence, or change in a chemical or ionic species, energy, or one or more physical properties (e.g., pH, pressure) at a site.

The secondary device can be integrated within each reservoir or placed in close proximity to the reservoirs. Secondary devices may comprise a complete device or system or may be one component of a larger or more complex device. In one embodiment, a sensor present inside a reservoir remains isolated from the surrounding environment until the permeability of the reservoir's barrier layer is altered. When it is desired to use the sensor, the barrier layer is removed or made permeable. The molecules to be detected that are present in the surrounding environment diffuse into the reservoir and interact with the sensor. In another embodiment, a light detection or imaging device (e.g., optical cell, CCD) chip. etc.) is located in a sealed reservoir until it is desired to detect an optical signal or capture an image. The barrier is removed or made permeable so that light energy can pass through to the optical device located in the reservoir.

Microchip devices also can store and expose any combination of chemicals and devices. For example, each reservoir can contain a different chemical or molecule for release. In one embodiment, devices can be placed outside of, but in close proximity to several chemical release reservoirs, in order to monitor when a chemical is released from a particular reservoir. In another embodiment, the chemical contained in the reservoir is an enzyme catalyst, glucose oxidase, which is used in some glucose sensing devices. It is also understood that multiple devices having completely different functions can be placed inside or near each reservoir of a microchip device. For example, in one embodiment, three sensors for detecting and quantifying three molecules can be located in the same reservoir, while three completely different sensors for detecting three different molecules can be placed in a neighboring reservoir. Alternatively, a single device may be comprised of three components, each of which is located in a different reservoir. With this technology, a microchip has the ability to selectively expose each chemical, device, or device component to the environment outside of the reservoir and to vary the number and type of chemicals and devices associated with each reservoir.

In a preferred embodiment, the secondary device is a sensor. Types of sensors that can be contained within or provided near a reservoir include biosensors, chemical sensors, physical sensors, or optical sensors. Preferred sensors measure properties such as biological activity, chemical activity, pH, temperature, pressure, optical properties, radioactivity, and electrical conductivity. These may be discrete sensors (e.g., "off-the-shelf" sensors) or sensors integrated into the substrate. Biosensors typically include a recognition element such as an enzyme or antibody. The transducer used to convert the interaction between the analyte and recognition element into an electronic signal may be, for example, electrochemical, optical, piezoelectric, or thermal in nature. Representative examples of biosensors constructed using microfabrication methods are described in U.S. Pat. Nos. 5,200,051; 5,466,575; 5,837,446; and 5,466,575 to Cozzette, et al.

There are several different options for receiving and analyzing data obtained with devices located in the microchip devices. First, the output signal from the device can be recorded and stored in writeable computer memory chips. Second, the output signal from the device can be directed to a microprocessor for immediate analysis and processing. Third, the signal can be sent to a remote location away from the microchip. For example, a microchip can be integrated with a radio transmitter in order to transmit a signal (e.g., data) from the microchip to a computer or other remote receiver source. The microchip can also be controlled using the same transmission mechanism. Power can be supplied to the microchip locally by a microbattery or remotely by wireless transmission.

Reacting Components

As used herein, unless explicitly indicated otherwise, the term "reacting component" includes any chemical species which can be involved in a reaction, including, but not limited to, reagents; catalysts, including enzymes, metals, and zeolites; proteins; nucleic acids; polysaccharides; polymers; cells, as well as organic or inorganic molecules, including diagnostic agents.

The reacting component contained within a reservoir may be present in any form (e.g., solid, liquid, gel, or vapor). They may be present in the reservoir in pure form or as a mixture with other materials. For example, the chemicals may be in the form of solid mixtures, such as amorphous and crystalline mixed powders, porous or nonporous monolithic solid mixtures, and solid interpenetrating networks; liquid mixtures or solutions, including emulsions, colloidal suspensions, and slurries; and gel mixtures, such as hydrogels. When the barrier layer is removed from a reservoir, the chemicals inside the reservoir can remain in the reservoir or can be released from the reservoir.

In one embodiment wherein the chemicals remain in the reservoir, the chemicals are zeolites used for a heterogeneous reaction. When the barrier layer is removed, the reagents diffuse into the reservoir to react at the surface of the zeolite catalyst, which remains in the reservoir. In one embodiment wherein the chemicals are released from the reservoir, molecules originally contained in the reservoir are released from the reservoir in vitro where the controlled release of a small (milligram to nanogram) amount of one or more molecules in a particular sequence is desired, for example, in the fields of analytic chemistry or medical diagnostics. Chemicals released in such a way can be effective as pH buffering agents, diagnostic agents, and reagents in complex reactions such as the polymerase chain reaction or other nucleic acid amplification procedures.

D. Barrier Layer

At least one opening of each reservoir of the microchip device is covered by a barrier layer, which separates (i.e. isolates) the contents of the reservoir from the surrounding environment or from portions thereof. The barrier layer can be impermeable, permeable, or semi-permeable to molecules or energy (e.g., light or electric field). The permeability of the barrier layer to molecules or energy can be actively controlled by the selective, real-time removal of all or part of the barrier layer by, for example, an applied stimulus (e.g., electric field or current, magnetic field, change in pH, or by thermal, photochemical, chemical, electrochemical, or mechanical means) or can be passively controlled by the barrier layer's structure, composition, or method of fabrication. For example, the passage of molecules or energy into each reservoir of a device can be controlled by diffusion (e.g., through a solid cap material, a nanoporous material, or a microporous material), osmotic pressure, ionic gradients, electric fields or currents, capillary forces, or surface tension.

The barrier layer can multi-layered. It can include a membrane, a reservoir cap, a plug, a thick or thin solid or semi-solid film, a two-phase interface (i.e. solid-liquid, liquid-liquid, or liquid-gas), or any other physical or chemical structure suitable for separating the contents of a reservoir from the environment outside of the reservoir. It generally is self-supporting across the reservoir opening. Selectively removing the barrier layer or making it permeable will then "expose" the contents of the reservoir to the environment (or selected components thereof) surrounding the reservoir.

In preferred embodiments, the barrier layer can be selectively disintegrated or permeabilized. As used herein, the term "disintegrate" is used broadly to include without limitation degrading, dissolving, rupturing, fracturing or some other form of mechanical failure, as well as a loss of structural integrity due to a chemical reaction or phase change, e.g., melting, in response to a change in temperature, unless a specific one of these mechanisms is indicated. As used herein, the term "permeabilization" includes without limitation any means of rendering the barrier layer porous or permeable in an amount effective to permit one or more species of molecules or forms of energy to pass in either direction through the barrier layer. Puncturing of the barrier layer, such as by injecting a needle through the barrier layer into the reservoir, generally is not a preferred means of permeabilizing or disintegrating the barrier layer.

In passive devices, the barrier layer is formed from a material or mixture of materials that degrade, dissolve, or disintegrate over time, or do not degrade, dissolve, or disintegrate, but are permeable or become permeable to molecules or energy. Barrier layer materials for passive microchips are preferably polymeric materials, but barrier layers can also be made of non-polymeric materials such as porous forms of metals, semiconductors, and ceramics. Representative examples of passive semiconductor barrier layer materials include nanoporous or microporous silicon membranes. Materials can be selected for use as barrier layers to give a variety of permeabilities or degradation, dissolution, or disintegration rates. To obtain different delay times (time required for the barrier layer to become permeable and "expose" the reservoir contents) using polymeric embodiments, barrier layers can be formed of different polymers, the same polymer with different thicknesses, degrees of crosslinking, or an ultra-violet (UV) light polymerizable polymer. In the latter case, varying the exposure of this polymer to UV light results in varying degrees of crosslinking and gives the barrier layer different diffusion properties (i.e. permeabilities) or degradation, dissolution, or disintegration rates. Another way to control the time at which the barrier layer becomes permeable is by using one polymer, but varying the thickness of that polymer. Thicker films of some polymers result in a delay in the time to barrier layer permeability. Any combination of polymer, degree of crosslinking, or polymer thickness can be modified to obtain a specific delay time. In one embodiment, the reservoir is covered by a degradable barrier layer that is nearly impermeable to the molecules of interest. The time to initiation of exposure of the reservoir contents will be limited by the time necessary for the barrier layer material to degrade. In another embodiment, the barrier layer is non-degradable and is permeable to specific molecules or types of energy (e.g., light) in the environment. The physical properties of the material used, its degree of crosslinking, its porosity, and its thickness will determine the time necessary for the molecules or energy to diffuse or pass through the barrier layer.

In active devices, the barrier layer can include any material that can be disintegrated or permeabilized in response to an applied stimulus (e.g., electric field or current, magnetic field, change in pH, or by thermal, chemical, electrochemical, or mechanical means). In a preferred embodiment, the barrier layer is a thin metal (e.g., gold) membrane and is impermeable to the surrounding environment (e.g., body fluids or another chloride containing solution). Based on the type of metal and the surrounding environment, a particular electric potential (e.g., +1.04 volts vs. a saturated calomel reference electrode) is applied to the metal harrier layer. The metal barrier layer oxidizes and dissolves by an electrochemical reaction, "exposing" the contents of the reservoir to the surrounding environment. In addition, materials that normally form insoluble ions or oxidation products in response to an electric potential can be used if, for example, local pH changes near the anode cause these oxidation products to become soluble. Examples of suitable barrier layer materials include metals such as copper, gold, silver, and zinc, and some polymers, as described, for example, in Kwon et al.,

*Nature,* 354:291-93 (1991); and Bac et al, *ACS Symposium Series,* 545: 98-110 (1994). In another embodiment, the barrier layer is a polymer with a melting point slightly above room temperature. When the local temperature near the polymer barrier layer is increased above the polymer's melting point by thin film resistors located near the barrier layer, the barrier layer melts and exposes the contents of the reservoir to the surrounding environment.

Any combination of passive or active barrier layers can be present in a single microchip device. Passive and active barrier layers can also be combined to form a multi-laminate or composite barrier layer. In one such embodiment, an impermeable, active barrier layer can be placed on top of a permeable, passive barrier layer. When it is desired to expose the contents of the reservoir to the surrounding environment, the impermeable, active barrier layer is removed by the application of a stimulus, such as an electric current. After the removal of the active barrier layer, the passive layer still remains over the reservoir. The passive barrier layer is permeable to the molecules in the surrounding environment. However, the rate at which molecules pass through the passive barrier layer was pre-determined during device fabrication by the choice of the material used for the passive barrier layer, its thickness, and its other physical and chemical properties.

E. Device Packaging, Control Circuitry, and Power Source

Active devices require actuation, which typically is done under the control of a microprocessor. The microprocessor is programmed to initiate the disintegration or permeabilization of the barrier layer in response to a variety of conditions, including a specific time, receipt of a signal from another device (for example by remote control or wireless methods), or detection of a particular condition using a sensor such as a biosensor.

Microelectronic device packages are typically made of an insulating or dielectric material such as aluminum oxide or silicon nitride. Low cost packages can also be made of plastics. Their purpose is to allow all components of the device to be placed in close proximity and to facilitate the interconnection of components to power sources and to each other. For in vivo applications of the microchip device, the entire package, including all components (i.e. the device, the microprocessor, and the power source), are coated or encapsulated in a biocompatible material such as poly(ethylene glycol) or polytetrafluoroethylene-like materials. The materials requirements for in vitro applications are typically less stringent and depend on the particular situation.

The control circuitry consists of a microprocessor, a timer, a demultiplexer, and an input source, for example, a memory source, a signal receiver, or a biosensor. Additional components can be added to the system depending on the desired mode of barrier actuation (e.g., thin film resistors for meltable barrier layers). The timer and demultiplexer circuitry can be designed and incorporated directly onto the surface of the microchip during electrode fabrication. The criteria for selection of a microprocessor are small size, low power requirement, and the ability to translate the output from memory sources, signal receivers, or biosensors into an address for the direction of power through the demultiplexer to a specific reservoir on the microchip device (see, e.g., Ji, et al., *IEEE J. Solid-State Circuits* 27:433-43 (1992)). Selection of a source of input to the microprocessor such as memory sources, signal receivers, or biosensors depends on the microchip device's particular application and whether device operation is preprogrammed, controlled by remote means, or controlled by feedback from its environment (i.e., biofeedback).

The criteria for selection of a power source are small size, sufficient power capacity, ability to be integrated with the control circuitry, the ability to be recharged, and the length of time before recharging is necessary. Batteries can be separately manufactured (i.e. off-the-shelf) or can be integrated with the microchip itself. Several lithium-based, rechargeable microbatteries are described in Jones & Akridge, "Development and performance of a rechargeable thin-film solid-state microbattery"*J. Power Sources,* 54:63-67 (1995); and Bates et al., "New amorphous thin-film lithium electrolyte and rechargeable microbattery", *IEEE 35$^{th}$ International Power Sources Symposium,* pp. 337-39 (1992). These batteries are typically only ten microns thick and occupy 1 $cm^2$ of area. One or more of these batteries can be incorporated directly onto the microchip device. Binyamin, et al., *J. Electrochem. Soc.,* 147:2780-83 (2000) describes work directed toward development of biofuel cells, which may provide a low power source suitable for the operation of the microchip devices described herein, as well as other microelectronic devices, in vivo.

II. Methods of Making the Microchip Devices

A. Fabrication of the Substrates with Reservoirs

Devices are manufactured using methods known in the art, reviewed for example, by Wolf et al. (1986), Jaeger (1988), and Madou, *Fundamentals of Microfabrication* (CRC Press 1997). The microchip devices can be made using the methods described below, alone or in combination with the methods described in U.S. Pat. Nos. 5,797,898 and 6,123,861, to Santini, et al.

In a preferred method of microchip manufacture, fabrication begins by depositing and photolithographically patterning a material, typically an insulating or dielectric material, onto the substrate to serve as an etch mask during reservoir etching. Typical insulating materials for use as a mask include silicon nitride, silicon dioxide, and some polymers, such as polyimide, In a preferred embodiment, a thin film (approximately 1000-3000 Å) of low stress, silicon-rich nitride is deposited on both sides of a silicon wafer in a Vertical Tube Reactor (VTR). Alternatively, a stoichiometric, polycrystalline silicon nitride ($Si_3N_4$) can be deposited by Low Pressure Chemical Vapor Deposition (LPCVD), or amorphous silicon nitride can be deposited by Plasma Enhanced Chemical Vapor Deposition (PECVD). Reservoirs are patterned into the silicon nitride film on one side of the wafer by ultraviolet photolithography and either plasma etching or a chemical etch consisting of hot phosphoric acid or buffered hydrofluoric acid. The patterned silicon nitride serves as an etch mask for the chemical etching of the exposed silicon by a concentrated potassium hydroxide solution (approximately 20-40% KOH by weight at a temperature of 75-90° C.). Alternatively, the reservoirs can be etched into the substrate by dry etching techniques such as reactive ion etching, deep trench etching, or ion beam etching. Use of these microfabrication techniques allows the incorporation of hundreds to thousands of reservoirs on a single microchip. The spacing between each reservoir depends on its particular application and whether the device is a passive or active device. Depending on the shape of the reservoirs and the sealing method used, the reservoirs of passive or active devices may be as little as a few microns apart. Reservoirs can be made in nearly any shape and depth, and need not pass completely through the substrate. In a preferred embodiment, the reservoirs are etched into a (100) oriented, silicon substrate by potassium hydroxide, in the shape of a square pyramid having side walls sloped at 54.7°, and pass completely through the substrate (approximately 300 to 600 μm thick) to the silicon nitride film on the other side of the substrate, forming a silicon nitride membrane. (Here, the silicon nitride film serves as a potassium hydroxide etch stop.) The pyramidal shape allows easy filling of the reservoirs with chemicals or devices through the large opening of the reservoir (approximately 500 µm by 500 µm for a 300 µm thick wafer) on the patterned side of the substrate, exposure through the small opening of the reservoir (approximately 50 µm by 50 µm) on the other side of the substrate, and provides a large cavity inside the device for storing reacting components and secondary devices.

Multi-portion substrate devices can be formed simply by making two or more individual substrate portions and then bonding them to one another with the matching openings of the reservoir portions aligned. There are two main types of bonds that can be formed between substrate portions. The first are atomic-scale or molecular-scale bonds. These types of bonds usually involve the interpenetration, intermixing, or interdiffusion of atoms or molecules of one or both of the substrates at the interface between the substrate materials. A preferred method of this type of substrate bonding for use primarily with silicon or glass substrates involves using heat and/or electric voltages to enable the interdiffusion of material between the two substrates, causing a molecular-scale bond to form at the interface between silicon, glass, and other similar materials. This anodic bonding process is well known to those skilled in the art. Another embodiment of this type of bonding involves melting and re-solidification of the top layer of one or both substrates. The melted material intermixes and upon solidification, a strong bond is formed between the two substrates. In one embodiment, this kind of melting and re-solidification can be caused by the brief application of a solvent, such as methylene chloride, to the substrate, such as poly(methyl methacrylate) or PLEXIGLAS™. The second type of bonding methods involves using a material other than the substrate material to form the bond. A preferred embodiment of this type of bonding includes the use of chemical adhesives, epoxies, and cements. An embodiment that can be used with UV transparent substrate materials involves UV curable epoxy. The UV curable epoxy is spread between the two substrate portions using a method such as spin coating, the reservoirs are aligned, and a UV light source is used to cross-link, or cure, the epoxy and bond the substrates together.

Alternatively, reservoirs can be formed using silicon-on-insulator (SOI) techniques, such as is described in Renard, *J. Micromech. Microeng.* 10:245-49 (2000). SOI methods can be usefully adapted to form reservoirs having complex reservoir shapes, for example, as shown in FIGS. 12A-C. SOI wafers behave essentially as two substrates that have been bonded on an atomic or molecular-scale before any reservoirs have been etched into either substrate. SOI substrates easily allow the reservoirs on either side of the insulator layer to be etched independently, enabling the reservoirs on either side of the insulator layer to have different shapes. The reservoirs on either side of the insulator layer can then be connected to make a single reservoir having a complex geometry by removing the insulator layer between the two reservoirs using methods such as reactive ion etching, laser, ultrasound, or wet chemical etching.

In other methods, the substrate is formed from polymer, ceramic, or metal for example by compression molding powders or slurries of polymer, ceramic, metal, or combinations thereof. Other forming methods useful with these materials include injection molding, thermoforming, casting, machining, and other methods known to those skilled in the art. Substrates formed using these methods can be formed (e.g., molded) to have the reservoirs or the reservoirs can be added in subsequent steps, such as by etching.

B. Fabrication of Passive Barrier Layers

In the fabrication of passive microchip devices, the barrier layer material is injected with a micro-syringe, printed with an inkjet printer cartridge, or spin coated into a reservoir having the thin membrane of insulating mask material still present over the small opening of the reservoir. If injection or inkjet printing methods are used, barrier layer formation is complete after the material is injected or printed into the reservoir and does not require further processing. If spin coating is used, the barrier layer material is planarized by multiple spin coatings. The surface of the film is then etched by a plasma, an ion beam, or chemical etchant until the desired barrier layer thickness is obtained. After deposition of the barrier layer material, and possibly after reservoir filling, the insulating mask material is removed, typically via dry or wet etching techniques. In a preferred embodiment, the insulating material used is silicon nitride and the barrier layer material is printed into the reservoir with an inkjet cartridge filled with a solution or suspension of the barrier layer material.

Barrier layers control the time at which secondary devices and/or reacting components are exposed to the surrounding environmental components or released from the reservoirs. Each barrier layer can be of a different thickness or have different physical properties to vary the time at which reservoir contents are exposed to the surrounding fluids. Injection, inkjet printing, and spin coating are preferred methods of reservoir filling and any of these methods may be used to fill reservoirs, regardless of the reservoir's shape or size. However, injection and inkjet printing are the preferred methods of filling deep (greater than 10 µm) reservoirs or reservoirs with large openings (greater than 100 µm). For example, to obtain different barrier layer thicknesses using injection or inkjet printing, different amounts of barrier layer material are injected or printed directly into each individual reservoir. Spin coating is the preferred method of filling shallow (less than 10 µm) reservoirs, reservoirs that do not pass completely through the substrate, or reservoirs with small (less than 100 µm) openings. Variation in barrier layer thickness or material by spin coating can be achieved by a repeated, step-wise process of spin coating, masking selected reservoirs, and etching. For example, to vary barrier layer thickness with spin coating, the barrier layer material is spin coated over the entire substrate. Spin coating is repeated, if necessary, until the material is nearly planarized. A mask material such as photoresist is patterned to cover the barrier layer material in all the reservoirs except one. Plasma, ion beam, or chemical etchants are used to etch the barrier layer material in the exposed reservoir to the desired thickness. The photoresist is then removed from the substrate. The process is repeated as a new layer of photoresist is deposited and patterned to cover the barrier layer material in all the reservoirs except one (the exposed reservoir is not the same one already etched to its desired thickness). Etching of the exposed barrier layer material in this reservoir continues until the desired barrier layer thickness is obtained. This process of depositing and patterning a mask material such as photoresist, etching, and mask removal can be repeated until each reservoir has its own unique barrier layer thickness. The techniques, such as UV photolithography, and plasma or ion beam etching, are well known to those skilled in the field of microfabrication.

Although injection, inkjet printing and spin coating are the preferred methods of barrier layer fabrication, it is understood that each reservoir can be capped individually by capillary action, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

C. Fabrication of Active Barrier Layers

In active devices, the barrier layer is located on, in, or covering each reservoir. The active barrier layers consist of any material that can be removed (e.g., disintegrated) or made permeable in response to an applied stimulus (e.g., electric field or current, magnetic field, change in pH, or by thermal, photochemical, chemical, electrochemical, or mechanical means). Examples of active barrier layer materials include metals such as copper, gold, silver, and zinc, and some polymers, as described, for example, in Kwon et al, *Nature,* 354: 291-93 (1991); and Bae et al., *ACS Symposium Series,* 545: 98-110 (1994). Barrier layers and any related circuitry are deposited, patterned, and etched using microelectronic and MEMS fabrication methods well known to those skilled in the art, reviewed, for example, by Wolf et al. (1986), Jaeger (1988), and Madou, *Fundamentals of Microfabrication* (CRC Press 1997). In addition, active barrier layers and associated circuitry can also be formed on the surface of microchip devices using microcontact printing and soft lithography methods, as described, for example, in Yan, et al., *J. Amer. Chem. Soc.,* 120:6179-80 (1998); Xia, et al., *Adv. Mater.,* 8(12):1015-17 (1996); Gorman, et al., *Chem. Mater.,* 7:52-59 (1995); Xia, et al., *Annu. Rev. Mater. Sci.,* 28:153-84 (1998); and Xia, et al., *Angew. Chem. Int. Ed.,* 37:550-75 (1998).

In a preferred embodiment, the barrier layer is defined using a lift-off technique. Briefly, photoresist is patterned in the form of electrodes on the surface of the substrate having the reservoirs covered by the thin membrane of insulating or dielectric material. The photoresist is developed such that the area directly over the covered opening of the reservoir is left uncovered by photoresist and is in the shape of an anode. A thin film of conductive material capable of dissolving into solution or forming soluble ions or oxidation compounds upon the application of an electric potential is deposited over the entire surface using deposition techniques such as chemical vapor deposition, electron or ion beam evaporation, sputtering, spin coating, and other techniques known in the art. Exemplary materials include metals such as copper, gold, silver, and zinc and some polymers, as disclosed by Kwon et al (1991) and Bae et al. (1994). After film deposition, the photoresist is stripped from the substrate. This removes the deposited film, except in those areas not covered by photoresist, which leaves conducting material on the surface of the substrate in the form of electrodes. An alternative method involves depositing the conductive material over the entire surface of the device, patterning photoresist on top of the conductive film using ultraviolet (UV) or infrared (IR) photolithography, so that the photoresist lies over the reservoirs in the shape of anodes, and etching the unmasked conductive material using plasma, ion beam, or chemical etching techniques. The photoresist is then stripped, leaving conductive film anodes covering the reservoirs. Typical film thicknesses of the conductive material may range from 0.05 to several microns. The anode serves as the active barrier layer and the placement of the cathodes on the device is dependent upon the device's application and method of electric potential control.

Following deposition of the electrodes, an insulating or dielectric material such as silicon oxide ($SiO_x$) or silicon nitride ($SiN_x$) is deposited over the entire surface of the device by methods such as chemical vapor deposition (CVD), electron or ion beam evaporation, sputtering, or spin coating. Photoresist is patterned on top of the dielectric to protect it from etching except on the cathodes and the portions of the anodes directly over each reservoir. The dielectric material can be etched by plasma, ion beam, or chemical etching techniques. The purpose of this film is to protect the electrodes from corrosion, degradation, or dissolution in all areas where electrode film removal is not necessary for release.

The electrodes are positioned in such a way that when a suitable electric potential is applied between an anode and a cathode, the unprotected (not covered by dielectric) portion of the anode barrier layer oxidizes to form soluble compounds or ions that dissolves into solution, compromising the barrier separating the reservoir contents from the surrounding environment.

D. Removal of the Insulator Membrane (Reservoir Etch Stop)

The thin membrane of insulating or dielectric material covering the reservoir used as a mask and an etch stop during reservoir fabrication must be removed from the active microchip device before filling the reservoir and from the passive microchip device (if the reservoir extends completely through the substrate) after filling the reservoir. The membrane may be removed in two ways. First, the membrane can be removed by an ion beam or reactive ion plasma. In a preferred embodiment, the silicon nitride used as the insulating material can be removed by a reactive ion plasma composed of oxygen and fluorine containing gases such as $CHF_3$, $CF_4$, or $SF_6$. Second, the membrane can be removed by chemical etching. For example, buffered hydrofluoric acid (BHF or BOE) can be used to etch silicon dioxide and hot phosphoric acid can be used to etch silicon nitride. If other materials are used as a membrane mask or etch stop, they can be removed using plasma compositions or chemicals known to those skilled in the art of etching.

E. Reservoir Filling and Sealing

The chemicals and devices to be stored and protected within the reservoirs are inserted into one of the openings of each reservoir (e.g., the large opening of square pyramid-shaped reservoirs). Chemicals can be inserted into the reservoir by injection, inkjet printing, or spin coating. Devices or device components can be fabricated inside or near each reservoir, or can be fabricated away from the microchip and inserted into or placed near a reservoir during microchip and packaging assembly. Each reservoir can contain different chemicals, devices, or device components.

The distribution over the microchip of reservoirs filled with the chemicals or devices of interest can vary. For applications in medical diagnostics, for example, ink jet printing can be used to fill each row of reservoirs on a microchip with different chemicals, each used to detect a particular analyte in solution. In another embodiment, each reservoir is filled with a slurry of catalyst particles by microinjection. If desired, each reservoir can be filled with a catalyst for a different chemical reaction. In yet another embodiment, a solution of a biological catalyst (i.e., enzyme) or a DNA marker molecule is injected into a reservoir and allowed to dry, immobilizing the enzyme or the DNA marker on the inner surface of the reservoir. Although injection, inkjet printing, and spin coating are the preferred methods of inserting chemicals into reservoirs, it is understood that each reservoir can be filled individually by capillary action, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

Each reservoir can also contain a different device or device component. Such devices can be fabricated directly in each reservoir. In one embodiment, thin metal electrodes for use in a sensing application can be fabricated onto the sidewalls of a pyramid-shaped reservoir using photolithography and electron beam evaporation. It is also possible to fabricate device components separately from the microchip and then integrate them with the microchip during the assembly process. In one embodiment, a device used in an optical based assay (e.g., LED) is placed into or near a reservoir during the assembly process. In another embodiment, a completely functional sensor (e.g., an ISFET or ion Selective Field Effect Transistor) is fabricated on another substrate portion. The substrate portion containing the sensor is aligned with the reservoir on the other substrate portion, and the two portions are bonded together, sealing the sensor inside the reservoir.

In preferred embodiments of both active and passive release devices, the reservoir openings used for chemical filling or device insertion (i.e. the openings opposite the barrier layer end) are sealed following reservoir filling, using any of a variety of techniques known in the art. For example, sealing can be provided by compressing a thin flexible film across the openings with a rigid backing plate. Alternatively, the opening can be sealed by applying a fluid material (e.g., an adhesive, wax, or polymer) that plugs the opening and hardens to form a seal. In another embodiment, a second substrate portion, e.g., of a second device, can be bonded across the reservoirs openings.

F. Device Packaging, Control Circuitry, and Power Source

The openings through which the reservoirs of passive and active devices are filled are sealed by compression, by wafer bonding, by a waterproof epoxy, or by another appropriate material impervious to the surrounding environment. For in vitro applications, the entire unit, except for the face of the device containing the reservoirs and barrier layers, is encased in a material appropriate for the system. For in vivo applications, the unit is preferably encapsulated in a biocompatible material such as poly(ethylene glycol) or polytetrafluoroethylene, or a case made of a biocompatible metal or ceramic.

The mechanism for exposing the reservoir contents of the device does not depend on multiple parts fitted or glued together which must retract or dislodge. Exposing of the contents of each reservoir can be controlled by a preprogrammed microprocessor, by remote control, by a signal from a biosensor, or by any combination of these methods.

A microprocessor is used in conjunction with a source of memory such as programmable read only memory (PROM), a timer, a demultiplexer, and a power source such as a microbattery, as described, for example, by Jones et al. (1995) and Bates et al. (1992), or a biofuel cell, as described by Binyamin, et al. (2000). A programmed sequence of events including the time a reservoir is to be opened and the location or address of the reservoir is stored into the PROM by the user. When the time for exposure or release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor. A microbattery provides the power to operate the microprocessor, PROM, and timer, and provides the electric potential input that is directed to a particular reservoir by the demultiplexer. The manufacture, size, and location of each of these components are dependent upon the requirements of a particular application. In a preferred embodiment, the memory, timer, microprocessor, and demultiplexer circuitry is integrated directly onto the surface of the chip. The microbattery is attached to the other side of the chip and is connected to the device circuitry by vias or thin wires. However, in some cases, it is possible to use separate, prefabricated, component chips for memory, timing, processing, and demultiplexing. In a preferred embodiment, these components are attached to the back side of the microchip device with the battery. In another preferred embodiment, the component chips and battery are placed on the front of or next to the microchip device, for example similar to how it is done in multi-chip modules (MCMs) and hybrid packages. The size and type of prefabricated chips used depends on the overall dimensions of the microchip device and the number of reservoirs.

Activation of a particular reservoir by the application of an electric potential or current can be controlled externally by remote control. Much of the circuitry used for remote control is the same as that used in the preprogrammed method. A signal, such as radio frequency (RF) energy, microwaves, low power laser, or ultrasound, is sent to a receiver by an external source, for example, computers or ultrasound generators. The signal is received by the microprocessor where it is translated into a reservoir address. Power is then directed through the demultiplexer to the reservoir having the appropriate address.

A biosensor can be integrated into or onto the microchip device to detect molecules in the surrounding fluids. When the concentration of the molecules reaches a certain level, the sensor sends a signal to the microprocessor to activate one or more reservoirs. The microprocessor directs power through the demultiplexer to the particular reservoir(s).

III. Applications for the Microchip Devices

Passive and active microchip devices have numerous in vitro and in vivo applications. The microchip devices can be used in a variety of applications in which it is desired to selectively expose molecules, devices, or a small volume (i.e. that of a reservoir) to another environment outside that volume. Applications include controlled or selective, on-demand sensing, for example to detect the presence or absence of a type of molecule, to test for biological activity or reactivity of molecules exposed to the sensor, or to measure parameters, such as pH, temperature, reactivity with another molecule, optical properties (e.g., refractive index, color, or fluorescence), radioactivity, pressure, or electrical conductivity. In one embodiment, the sensor employs an optical fiber that can be used to sense changes in optical properties in or near the reservoirs, changes which might occur, for example, due to a reaction in the reservoir or in the environment adjacent the reservoir. In a related embodiment, the reservoir contains a scintillation fluid to aid in the (optical) detection of radioactive materials.

In a preferred embodiment, the microchip device contains one or more sensors for use in glucose monitoring and insulin control. For example, one or more reservoirs could contain a sensor while other reservoirs contain insulin for release. Information from the sensor could be used to actively control insulin release.

The microchip device can be used in vitro to selectively expose secondary devices or device components, reacting components, or both to the surrounding environment or components thereof. For some in vitro applications, the microchip can release small, controlled amounts of chemical reagents or other molecules into solutions or reaction mixtures at precisely controlled times and rates. In others, small devices such as sensors can be protected from the surrounding environment until they are needed. Analytical chemistry and medical diagnostics are examples of fields where microchips having the ability to selectively expose chemicals and devices can be used. Such microchips can also be used in vivo as delivery devices. The microchips can be implanted into a patient, either by surgical techniques or by injection, or can be swallowed. The microchips can provide delivery or sensing of many different molecules and devices at varying rates and at varying times. Other microchips can be used to catalyze a particular reaction in vivo. For example, the catalyst (i.e. enzyme) can be protected in the reservoir from the surrounding environment until it is desired to expose the enzyme and catalyze the reaction of interest.

The devices also can be used to isolate a reaction component, such as enzymes and other catalysts, for example in analytical chemistry or medical diagnostics. For example, the reservoir can function as a packed bed reactor or immobilized enzyme reactor. In one embodiment, the devices utilize osmotic pressure and/or swellable materials to open the reservoirs to permit molecules to enter or leave the reservoirs. These and other applications are detailed in the non-limiting embodiments described below, wherein it is understood that the number, geometry, and placement of each reservoir, barrier layer, or other object (i.e., heaters, electrodes, channels, etc.) in or near each reservoir can be modified for a particular application. For simplicity, only one or two reservoirs are shown in each Figure. However, it is understood that a microchip component or device would contain at least two, and preferably many more, reservoirs arrayed across a substrate.

A. Selective Sensing Device

Figure 2A:
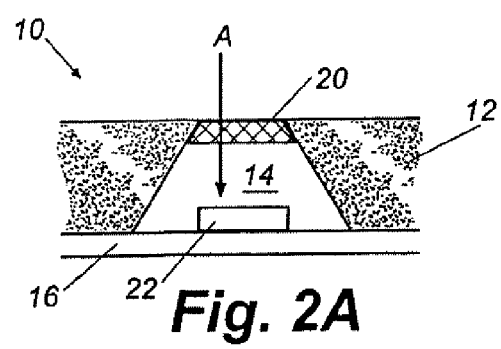
FIGS. 2A-C are cross-sectional diagrams showing a device having a reservoir covered by a semi-permeable barrier layer which permits passage of molecule A into or out of the reservoir (FIG. 2A), wherein the reservoir initially is covered by another, impermeable barrier layer (FIG. 2B) until the barrier layer is selectively removed (FIG. 2C).
Figure 2B:
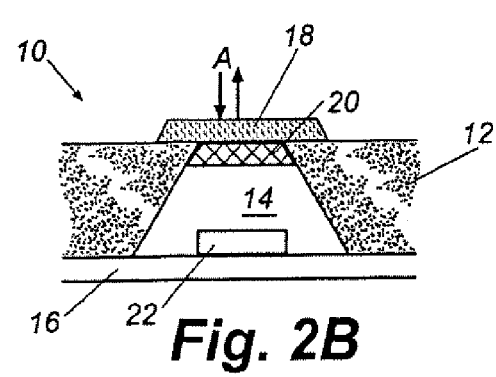
Figure 2C:
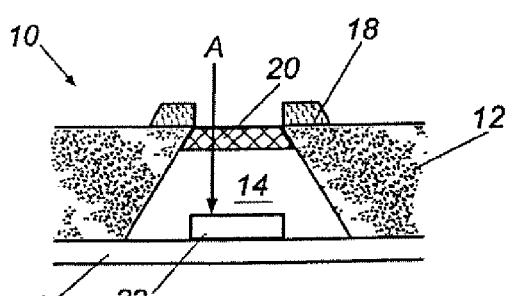

In one embodiment, illustrated in FIGS. 2A-C, a sensor 22 for detecting a particular molecule is fabricated or placed at the bottom or on an interior side of a reservoir 14 in substrate 12 of microchip device 10, having backing plate 16 and semi-permeable barrier layer 20. In FIG. 2A, barrier layer 20 covers the reservoir, allowing the passage of molecule of interest "A" into or out of the reservoir 14 while restricting the passage of other molecules or materials (e.g., cells or cellular components) that may affect the sensing of the molecule of interest. When the microchip device is first placed into operation, the semi-permeable barrier layer 20 can be directly in contact with the surrounding environment, or it can be covered by another barrier layer 18 that is impermeable to molecule "A", as shown in FIG. 2B. In the latter case, the impermeable barrier layer 18 prohibits the passage of material into or out of the reservoir 14 until the impermeable barrier layer 18 is partially or completely removed, as shown in FIG. 2C, at which time the sensor 22 can then sense the presence or absence of molecule of interest "A".

When the impermeable barrier layer can be partially or completely removed by the application of a stimulus (e.g., electric potential), the operator or user of the microfabricated device has the ability to initiate the operation of the sensor on demand. Such components or devices could be useful in applications where sensor operation or performance is diminished by exposure to a particular environment. For example, the performance of some implantable sensors has been observed to diminish as they become coated or "fouled" with cells, proteins, and other components found in vivo or in other operating environments.

B. Optical Sensing Device

Figure 3A:
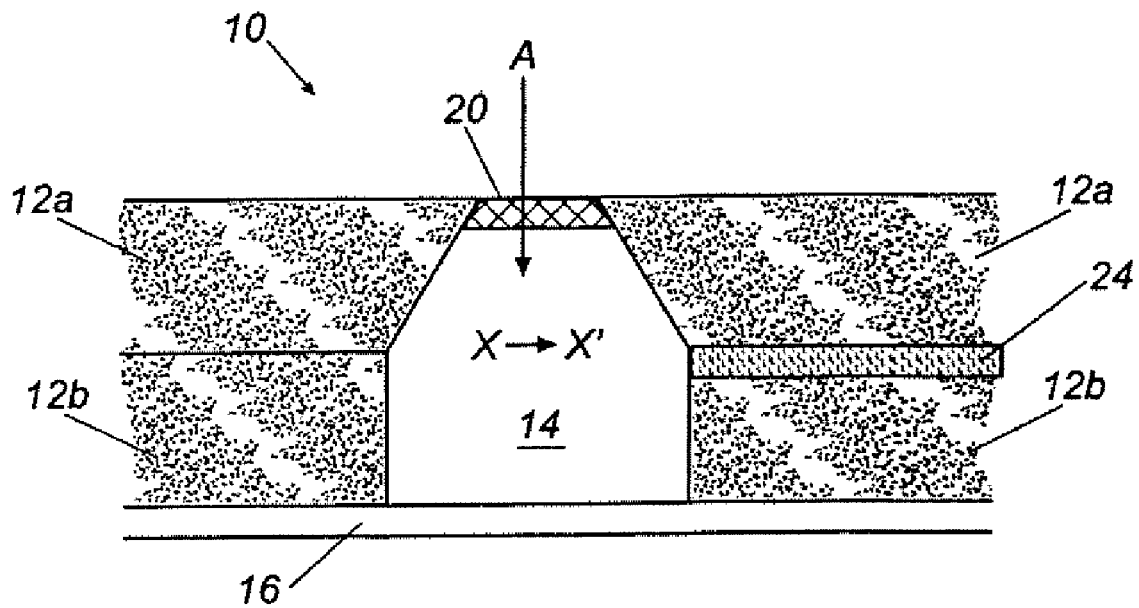
FIGS. 3A-B are cross-sectional diagrams of two embodiments of an optical sensing device, wherein the device includes an optical fiber inside (FIG. 3A) or outside and over (FIG. 3B) a single reservoir covered by a semi-permeable barrier layer which permits passage of molecule A into or out of the reservoir.
Figure 3B:
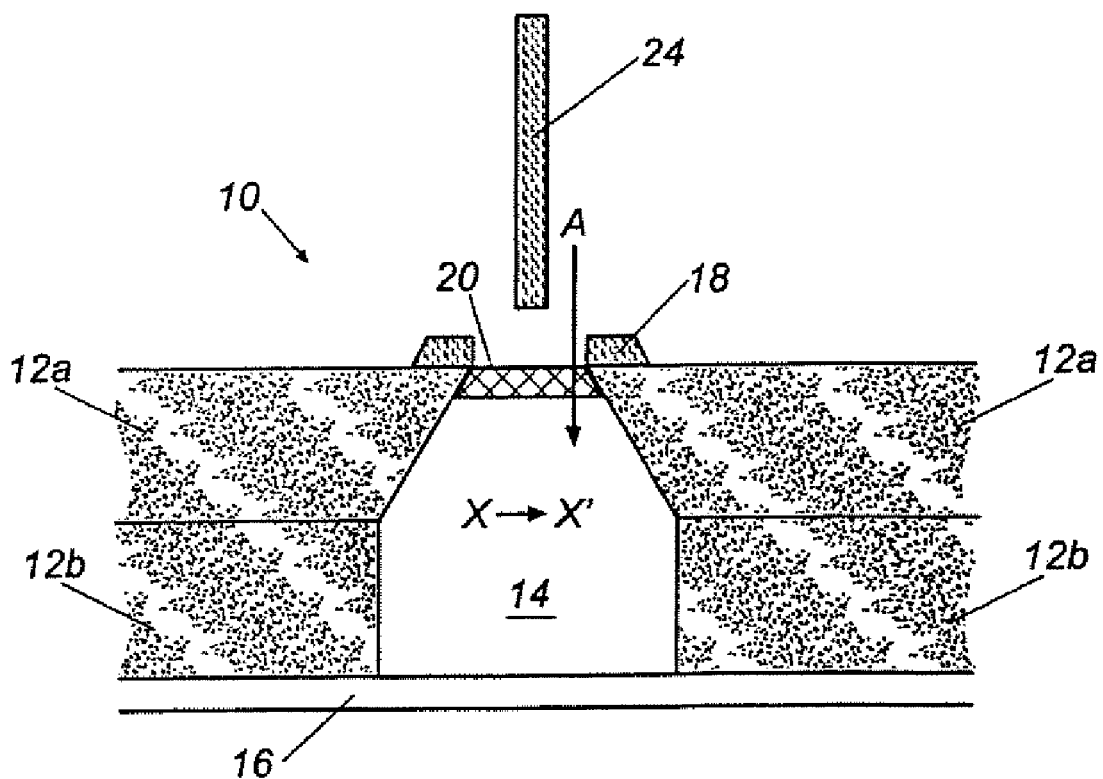

In another embodiment, illustrated in FIGS. 3A-B, a miniature optical fiber 24 is placed in or near a reservoir 14 disposed in substrate portions 12a and 12b of microchip device 10, having semi-permeable barrier layer 20 and backing plate 16. Reservoir 14 contains one or more substances "X" that interact with one or more molecular or cellular component of interest "A", present in the environment around the microchip device (outside the reservoir). As shown in FIG. 3B, the substance X inside the reservoir 14 is exposed by the partial removal of an initially present barrier layer 18 to the environment containing the molecule or cellular component of interest "A". Then an optical property of the substance inside reservoir 14 changes (X→X') and is sensed via optical fiber 24. For example, the optical fiber 24 may be used to expose the contents of the reservoir 14 to a light source, possibly of a single wavelength. The optical fiber 24 also can have the ability to detect and measure changes in fluorescence, or some other optical phenomenon. The excitation light source or detection source can be integrated into the reservoir (FIG. 3A) or positioned externally from to the reservoir (FIG. 3B). Such components or devices could be useful in making colorimetric diagnostic devices for the examination of both biological (e.g., proteins or DNA fragments) and non-biological substances.

C. Selective Sensor Device with Reagents

In another embodiment, illustrated in FIGS. 4-5, the reservoirs of the microchip device contain a combination of reagents and sensors in various configurations. For example, a reservoir containing one or more sensors can be filled with one or more reagents or other chemicals required for conducting a particular assay.

Figure 4A:
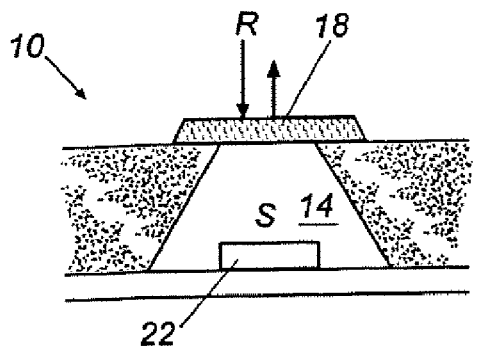
FIGS. 4A-B are cross-sectional diagrams illustrating a device having a reservoir containing both a sensor and a chemical reagent, with an intact (FIG. 4A) and partially removed (FIG. 4B) impermeable barrier layer.
Figure 4B:
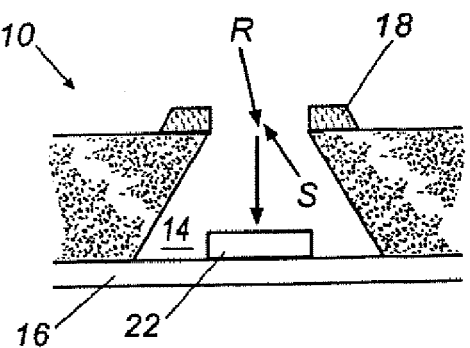

FIG. 4A shows microchip device 10 having reservoir 14 that contains sensor 22 and chemical reagent "S", with reservoir 14 covered by barrier layer 18. The barrier layer 18 isolates sensor 22 and chemical reagent "S" from the environment outside the reservoir. The environment contains or potentially contains molecule of interest "R". As shown in FIG. 4B, when it is desired to activate the sensors, the barrier layer 18 is at least partially removed, to permit the molecule of interest "R" to react with chemical reagent "S" to produce product T, which is sensed by sensor 22. The chemical reagent "S", which is necessary for the assay may remain in the reservoir 14 after the barrier layer is removed, or may slowly pass out of the reservoir 14 while the molecule of interest "R" enters the reservoir 14. In other words, it is not critical whether the assay reaction occurs inside or just outside of the reservoir, so long as the reaction product can be sensed by the sensor.

Figure 5A:
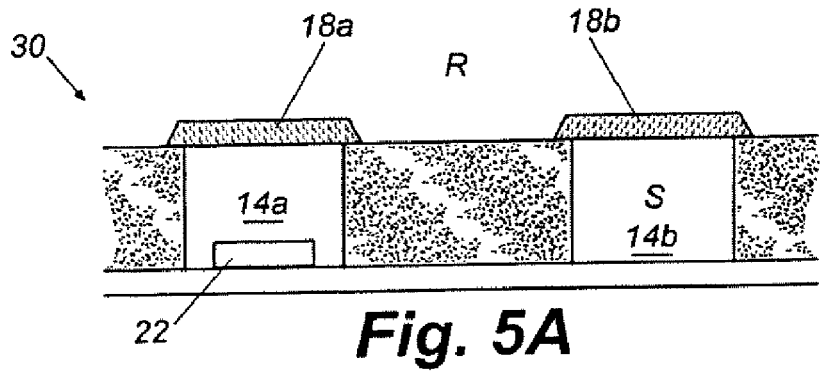
FIGS. 5A-B are cross-sectional diagrams illustrating a device having one reservoir which contains a sensor and another reservoir which contains a chemical reagent, with an intact (FIG. 5A) and partially removed (FIG. 5B) impermeable barrier layers over the reservoirs.
Figure 5B:
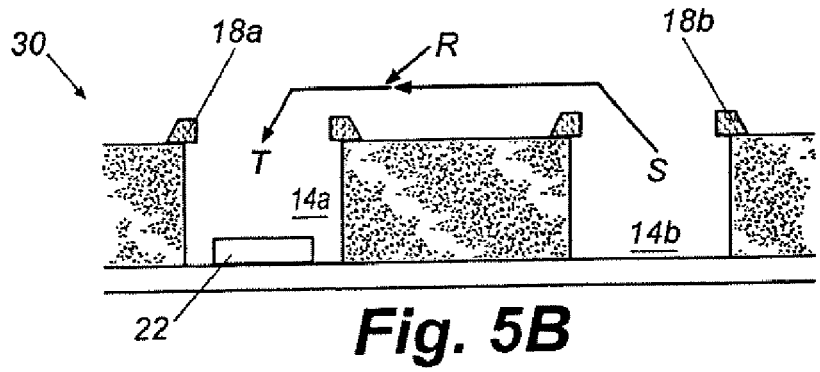

In a variation of this embodiment, illustrated in FIG. 5A, microchip device 30 includes sensor 22 in a first reservoir 14a and chemical reagent "S" in one or more neighboring reservoirs 14b, covered by barrier layers 18a and 18b, respectively. As shown in FIG. 5B, sensing is initiated by removing barrier layers 18a and 18b to open reservoirs 14a and 14b, which exposes sensor 22 and chemical reagent "S" to the environment outside the reservoirs, which includes molecule of interest "R". Chemical reagent "S" passes out of reservoir 14b, reacts molecule of interest "R" to produce product T, which then is sensed by sensor 22 in reservoir 14a.

Figure 6:
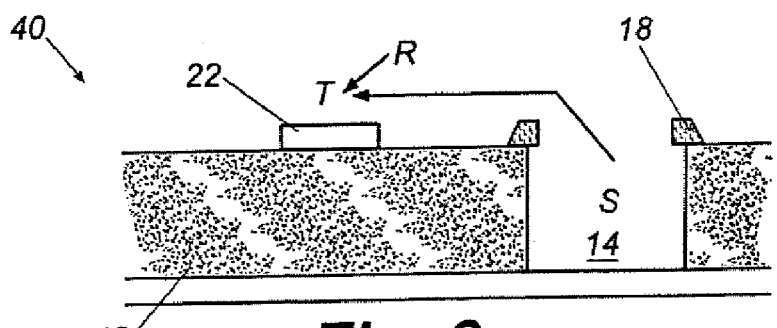
FIG. 6 is a cross-sectional diagram illustrating a device having a reservoir containing a chemical reagent and a sensor located on the substrate outside of the reservoir.

Alternatively, in certain applications, the sensor need not be located within a reservoir. For example, as shown in FIG. 6, microchip device 40 includes reservoir 14 disposed in substrate 12 and containing chemical reagent "S". Sensor 22 is mounted on an exterior surface of substrate 12. Again sensing is initiated by removing barrier layer 18 (shown in partially removed form), thereby permitting chemical reagent "S" to exit reservoir 14 and react with molecule of interest "R" to produce product T, which then is sensed by sensor 22. It is evident that the assay in these examples cannot be initiated until the barrier layer is disintegrated or permeabilized and the sensor, reagents, and molecule of interest are no longer isolated from one another.

D. Control of Sensor Devices

Figure 7:
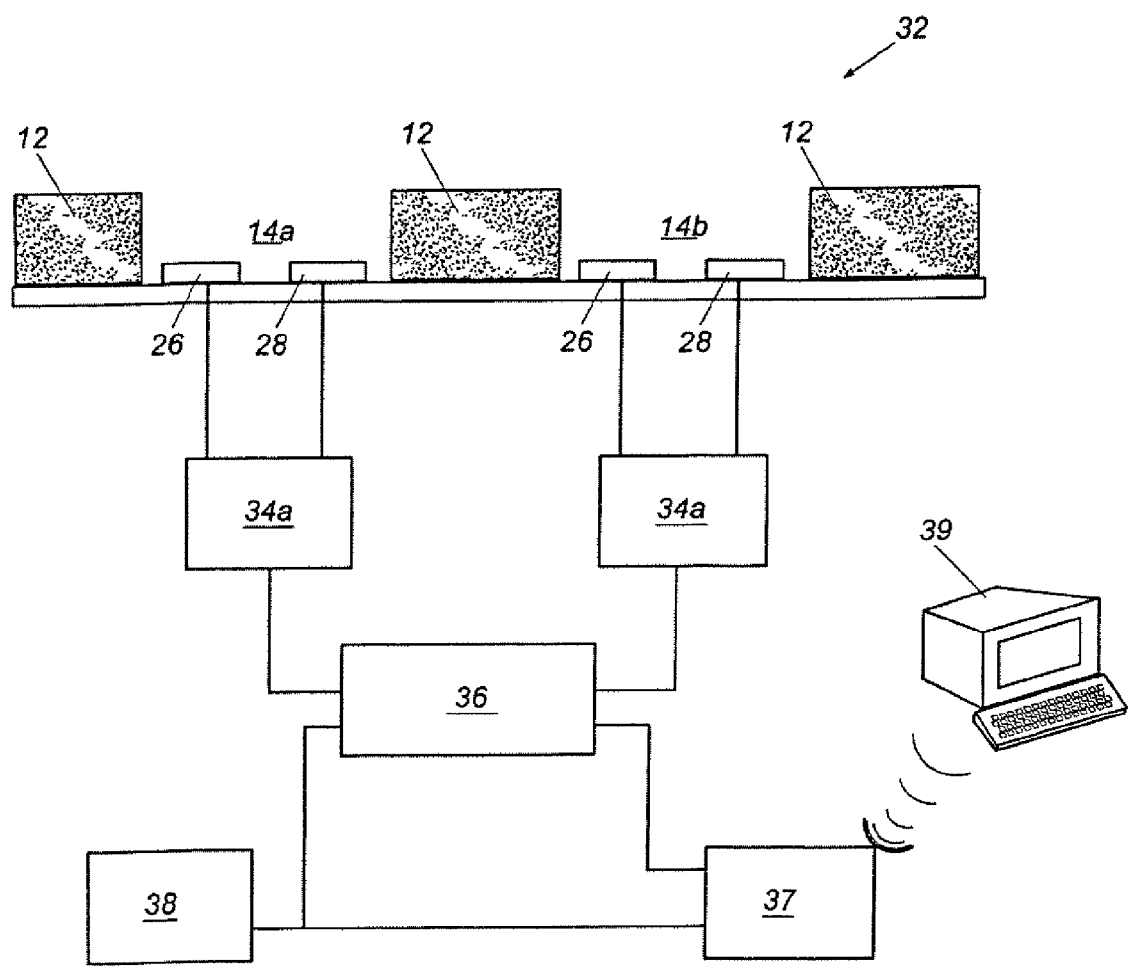
FIG. 7 is a process flow diagram illustrating one embodiment for controlling and communicating with sensors located in reservoirs of a microchip device.

In one embodiment, illustrated in FIG. 7, a microchip device 32 contains two reservoirs, 14a and 14b, with each containing two sensors: reference sensor 26 and sensor 28. Reference sensor 26 is used to check the operation of sensor 28 in each reservoir. A microprocessor 36, powered by power source 38, can be programmed to continuously compare, using comparison units 34a or 34b, (e.g., voltmeters or other instrumentation), the operation of sensor 28 to the reference sensor 26 in reservoir 14a or 14b. If for example sensor 28 in reservoir 14a is not operating properly, a signal can be sent back to the microprocessor 36. The microprocessor 36, in turn, can activate reservoir 14b and expose the new pair of electrodes (i.e. sensor 28 and reference sensor 26 in reservoir 14b. In addition, the microprocessor 36 can send a signal to a transmitter 37 to notify a remotely located computer 39 that only one good sensor remains, or to signal other operational information. While the Figure shows the reservoirs as open, it is understood that the one or more of the reservoirs can be provided in an initially closed state, that is covered by a barrier layer until exposure is desired.

E. Packed Bed Reactor

In another embodiment, the microchip device serves as a packed bed reactor, an example of which is illustrated in FIGS. 8A and 8B. For example, microchip device 50 includes a reservoir disposed in substrate 12 and filled with catalyst 52. Catalyst 52 can be any catalytic material or can be an inert, porous support coated with the catalytic material. The reservoir is covered by barrier layer 18, which prohibits or restricts the passage of reactants "A" to the catalyst or products away from the catalyst, as shown in FIG. 5A. Complete or partial removal, or permeabilization, of the barrier layer 18 exposes catalyst 52 to the environment outside of the reservoir and allows reactants "A" to contact the catalyst 52 and react to form product B, as shown in FIG. 5B.

Microchip device 50 optionally is provided with reaction control component 54 positioned within the reservoir. Examples of these reaction control components include resistive heaters and polarizable electrodes. These control components can be mounted in (e.g., on a bottom or side interior surface) or near the reservoir to assist in controlling the rate of the reaction (A→B). FIGS. 8C and 8D show are top views of a resistive heater and a polarized electrode, respectively, located on the bottom of reservoir.

It is understood that a permeable or semi-permeable barrier layer also can be used in addition to or in place of an impermeable barrier layer to limit or control the types of molecules allowed to contact the catalyst.

These microchip device reactors may be particularly useful in applications where prolonged exposure of the catalyst to the environment results in decreased performance of the catalyst due to "fouling" or coating of the catalyst surface or due to chemical degradation of the catalyst, because these devices would enable many discrete quantities of catalyst to be contained in one small device, with each quantity available independently when needed. For example, if the catalyst of a first reservoir becomes fouled, then a second reservoir can be opened to expose fresh catalyst, and repeated for any number of reservoirs. Furthermore, different catalysts can be provided in different reservoirs of a single device, thereby enhancing the range of reactions that can be catalyzed with a single device.

F. Immobilized Enzyme Reactor

Figure 9A:
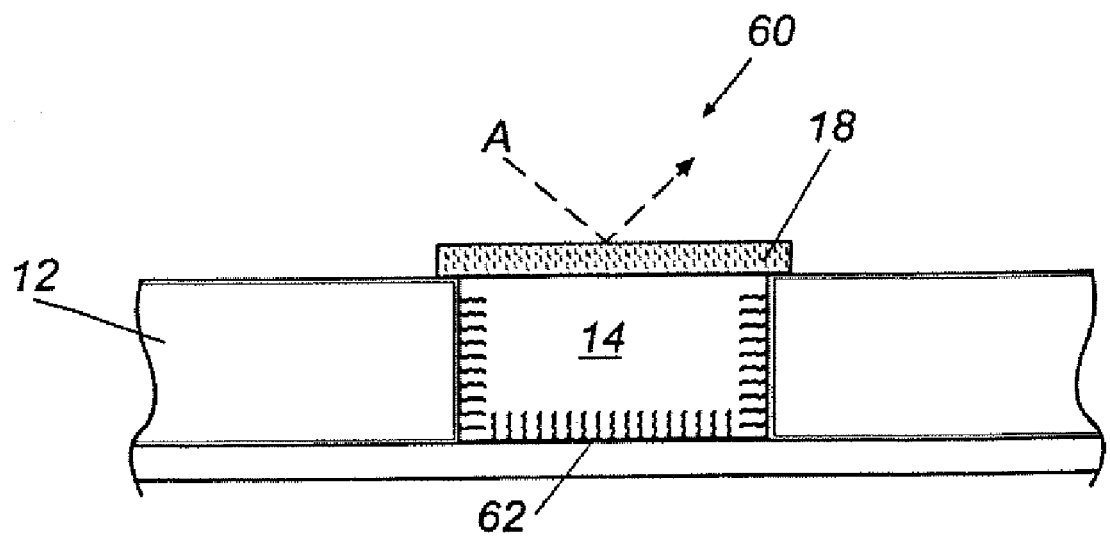
FIGS. 9A-B are cross-sectional diagrams illustrating a device having a reservoir containing an immobilized enzyme, with the intact barrier layer impermeable to reactant A (FIG. 9A) and the barrier layer partially removed and permitting reactant A to contact the immobilized enzyme to yield product B (FIG. 9B).
Figure 9B:
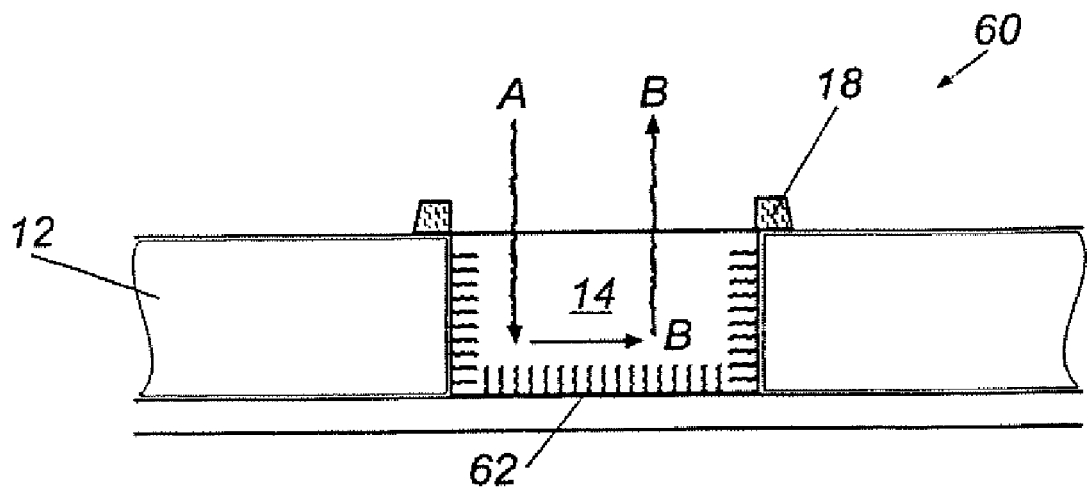

In still another embodiment, the reservoirs of the microchip device are provided with an immobilized enzyme. For example, as illustrated in FIGS. 9A-B, microchip device 60 includes reservoir 14 disposed in substrate 12 and covered by barrier layer 18. An enzyme 62 is immobilized on one or more of the surfaces inside reservoir 14. Barrier layer 18 covers the reservoir to isolate the enzyme 62 from the environment which includes reactant "A". As illustrated in FIG. 9B, complete or partial removal of barrier layer 18 exposes immobilized enzyme 62 to reactant "A", which reacts to form product "B".

Alternatively or in addition, one or more microorganisms (e.g., yeast, pyruvate) can be coated or immobilized on surfaces inside or near a reservoir. For example, the microorganism may react with or catalyze a reaction involving a molecular species that is undetectable by the sensor until reacted the microorganism to produce a second, detectable molecular species.

It is understood that a permeable or semi-permeable barrier layer also can be used in addition to or in place of an impermeable barrier layer to limit or control the types of molecules allowed to contact the immobilized enzyme. These microchip reactor devices can be useful in applications where a highly selective enzyme is required, but the stability of the enzyme is decreased when exposed to a particular environment for prolonged periods of time.

G. Use of Osmotic Pressure and/or Swellable Materials

In one embodiment, reservoirs are opened by rupture of one or more barrier layers initially covering the reservoirs. In one variation of this embodiment, rupture is initiated by employing osmotic pressure, water swellable materials, or combinations thereof. For example, a reservoir in a microchip device can be filled or coated with a material (for example, a salt) that causes an osmotic pressure to develop when exposed to materials from the environment outside or near the reservoir. Depending on the design of the reservoirs, the osmotic pressure generating materials selected, and the placement of the osmotic pressure generating materials in or near the reservoir, the osmotic pressure that would develop can be used to either pull material into the reservoir or expel material from the reservoir.

Figure 10:
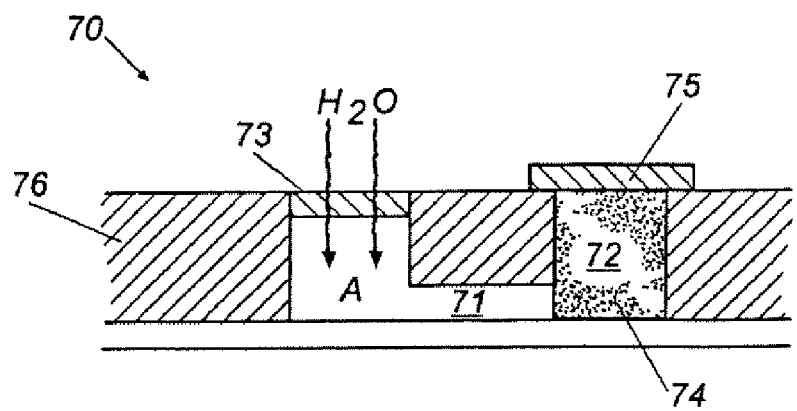
FIG. 10 is a cross-sectional diagram of one embodiment of a device utilizing osmotic pressure forces generated within a first reservoir to rupture a barrier layer covering a second, nearby reservoir.

One example of the use of osmotic pressure in microchip components or devices, illustrated in FIG. 10, involves using the osmotic pressure generated in a reservoir to eject a chemical from the reservoir or from a neighboring reservoir. In FIG. 10, microchip device 70 includes substrate 76, first reservoir 72 containing chemicals to be released 74, and second reservoir 71 containing a concentrated solution of ionic species "A" (the osmotic pressure generating material). The device further includes semi-permeable barrier layer 73 through which water or other solvent for "A" can pass, and rupturable, impermeable barrier layer 75. Semi-permeable barrier layer 73 optionally can be covered by another impermeable barrier layer (not shown) that can be selectively removed to expose barrier layer 73 to the surrounding environment. FIG. 10 shows water permeating barrier layer 73 due to osmotic forces. More specifically, the concentration of ionic species "A" in reservoir 71 is greater that the concentration of ionic species "A" in the aqueous environment, thereby driving water through barrier layer 73 to equalize the concentration of species "A". This increased quantity of water in reservoir 71 increases the pressure in reservoirs 71 and 72, until the pressure causes impermeable barrier layer 75 to rupture and release chemicals 74. Reservoirs 71 and 72 may be separated by a flexible, fluid-tight membrane or any other means which allows a change in the pressure of one reservoir to affect the pressure in the other, but which maintains the separation of the contents of each reservoir.

Figure 11A:
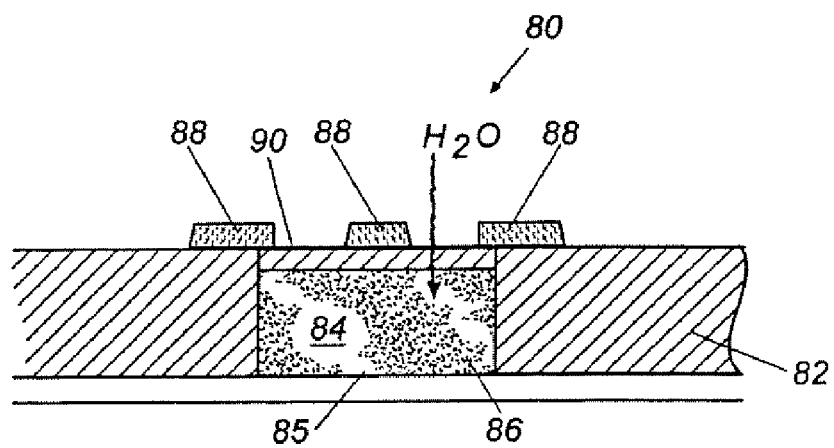
FIGS. 11A-B are cross-sectional diagrams illustrating a device having a barrier layer covering a reservoir that contains both an osmotic pressure generating material and a chemical to be released (FIG. 11A) and the rupture of the barrier layer due to a pressure differential produced by osmotic forces (FIG. 11B).
Figure 11B:
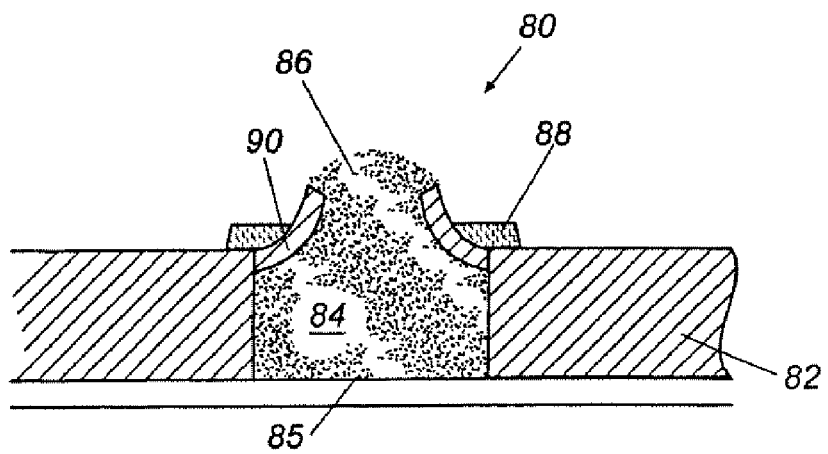

In another variation of this embodiment, an osmotic pressure generating material and a chemical that is meant to be ejected or released from the reservoir are placed in the same reservoir. An example is illustrated in FIGS. 11A-B, which shows microchip device 80 including reservoir 84 disposed in substrate 82 and covered by rupturable, semi-permeable barrier layer 90. Reservoir 84 is filled with chemical to be released 86 and osmotic pressure generating material 85. Filled reservoir 84 initially is covered with an impermeable barrier layer 88 to keep the surrounding solution from entering the reservoir before release from the reservoir is desired. When release is desired, a stimulus is applied to the impermeable barrier layer 88 long enough to expose semi-permeable barrier layer 90 and render it permeable to a solution outside of the reservoir 84, as shown in FIG. 11A. The solution (shown as $H_2O$) then passes through the barrier layer due to the osmotic pressure difference (i.e., driving force) between the environment inside and outside of reservoir 84, for example due to different ion or salt concentrations. The pressure in reservoir 84 increases due to the flow of solution into the reservoir 84 until the increased pressure causes the semi-permeable barrier layer 90 and the remainder of impermeable barrier layer 88 to rupture, thus causing the contents of the reservoir, chemicals 86 and osmotic pressure generating material 85, to be released into the surrounding solution as illustrated in FIG. 11B.

In an alternative but similar embodiment, a swellable material can be used in place of the osmotic pressure generating material in the reservoir. The swellable material, such as a swellable polymer, will swell or expand when exposed to a particular solution. The reservoir volume, barrier layer material and thickness, and swellable material type and volume, can be selected to provide a system in which the swelling of the swellable material causes the barrier layer to rupture in much the same way that the buildup of solution in the reservoir due to osmotic pressure caused the barrier layer to rupture in the preceding example. Various combinations of semi-permeable and impermeable barrier layers can be used depending on the particular application and microchip device design.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method of detecting an analyte in vivo comprising:
   implanting at a site in a patient a device which comprises:
   one or more discrete reservoirs each containing at least one reacting component,
   at least one non-degradable barrier layer covering an opening in each of the one or more discrete reservoirs, the non-degradable barrier layer being selectively permeable to an analyte to be detected, wherein the reacting component remains inside the reservoirs, and
   a degradable barrier layer, which is impermeable to the analyte to be detected and which covers the at least one non-degradable barrier layer over the reservoir opening;
   disintegrating or permeabilizing the degradable barrier layer over at least one of the reservoirs to permit the analyte at the site to enter the reservoir and react with the at least one reacting component; and
   using a sensor positioned externally from the reservoir to detect the reaction between the reacting component and the analyte.

2. The method of claim 1, wherein the detecting comprises imaging or optical detection.

3. The method of claim 1, wherein the at least one non-degradable barrier layer comprises a semi-permeable polymeric membrane.

4. The method of claim 1, wherein the at least one non-degradable barrier layer comprises a nanoporous or microporous silicon membrane.

5. The method of claim 1, wherein the non-degradable barrier layer is in the form of a plurality of discrete reservoir caps.

6. The method of claim 1, wherein the degradable barrier layer comprises a biodegradable polymeric material.

7. The method of claim 1, wherein the degradable barrier layer comprises a metal film and the device further includes a power source and control circuitry for disintegrating the degradable barrier layer.

8. The method of claim 1, wherein the reaction between the reacting component and the analyte to be detected is a binding reaction.

9. A method of detecting an analyte in vivo comprising:
   implanting at a site in a patient a device which comprises:
   a plurality of discrete reservoirs located in a substrate, each reservoir having at least one opening,
   at least one reacting component contained in each reservoir,
   at least one non-degradable barrier layer, which is permeable to an analyte to be detected and covers each reservoir opening, wherein the reacting component remains inside the reservoirs, and
   a degradable barrier layer, which is impermeable to the analyte to be detected and which covers the at least one non-degradable barrier layer over the reservoir opening; and
   disintegrating or permeabilizing the at least one degradable barrier layer to permit the analyte at the site to enter the reservoirs and undergo a binding reaction with the at least one reacting component; and
   using a sensor positioned externally from the reservoir to detect the binding reaction between the reacting component and the analyte.

10. The method of claim 9, wherein the substrate comprises a polymer.

11. The method of claim 9, wherein the at least one degradable barrier layer comprises a biodegradable polymeric material.

12. The method of claim 9, wherein the at least one degradable barrier layer comprises a metal film and the device further includes a power source and control circuitry for disintegrating the degradable barrier layer.

13. The method of claim 9, wherein the at least one non-degradable barrier layer comprises a semi-permeable polymeric membrane.

14. The method of claim 9, wherein the at least one non-degradable barrier layer comprises a nanoporous or microporous silicon membrane.

15. A method of detecting an analyte in vivo comprising:
   implanting in a patient a device which comprises:
   a plurality of discrete reservoirs located in a substrate, each reservoir having at least one opening,
   at least one non-degradable barrier layer which comprises a semi-permeable polymeric membrane, which is permeable to an analyte to be detected and which covers each reservoir opening,
   a degradable barrier layer, which is impermeable to the analyte to be detected and which covers the at least one non-degradable barrier layer over the reservoir opening, and
   at least one reacting component which remains contained inside each of the reservoirs and can undergo a binding reaction with the analyte,
   passively or actively degrading the at least one degradable barrier layer to permit the analyte to enter the reservoirs and react with the at least one reacting component; and using a sensor positioned externally from the reservoir to detect the reaction between the reacting component and the analyte.

16. The method of claim 15, wherein the degradable barrier layer comprises a biodegradable polymeric material.

17. The method of claim 15, wherein the degradable barrier layer comprises a metal film and the device further includes a power source and control circuitry for disintegrating the degradable barrier layer.

18. The method of claim 15, wherein the substrate comprises a polymer.

19. The method of claim 15, wherein the step of detecting comprises imaging or optical detection.

20. The method of claim 1, wherein the reacting component is selected from the group consisting of metals, proteins, nucleic acids, cells, and combinations thereof.

21. The method of claim 9, wherein the reacting component is selected from the group consisting of metals, proteins, nucleic acids, cells, and combinations thereof.

22. The method of claim 15, wherein the reacting component is selected from the group consisting of metals, proteins, nucleic acids, cells, and combinations thereof.

* * * * *